US010028651B2

(12) United States Patent
Tesar

(10) Patent No.: US 10,028,651 B2
(45) Date of Patent: Jul. 24, 2018

(54) SURGICAL VISUALIZATION SYSTEMS AND DISPLAYS

(71) Applicant: CAMPLEX, INC., Germantown, TN (US)

(72) Inventor: John Tesar, Tucson, AZ (US)

(73) Assignee: CamPlex, Inc., Germantown, TN (US)

(*) Notice: Subject to any disclaimer, the term of this patent is extended or adjusted under 35 U.S.C. 154(b) by 226 days.

(21) Appl. No.: 14/491,827

(22) Filed: Sep. 19, 2014

(65) Prior Publication Data
US 2015/0085095 A1    Mar. 26, 2015

Related U.S. Application Data

(60) Provisional application No. 61/880,808, filed on Sep. 20, 2013, provisional application No. 61/920,451, (Continued)

(51) Int. Cl.
*H04N 7/18* (2006.01)
*A61B 1/313* (2006.01)
(Continued)

(52) U.S. Cl.
CPC .......... *A61B 1/3132* (2013.01); *A61B 1/005* (2013.01); *A61B 1/00154* (2013.01); (Continued)

(58) Field of Classification Search
IPC .................................................. A61B 1/3132
See application file for complete search history.

(56) References Cited

U.S. PATENT DOCUMENTS

| 497,064 A | 5/1893 | Van Meter |
|---|---|---|
| 2,826,114 A | 3/1958 | Bryan |

(Continued)

FOREIGN PATENT DOCUMENTS

| CN | 2336380 Y | 9/1999 |
|---|---|---|
| CN | 101518438 | 9/2009 |

(Continued)

OTHER PUBLICATIONS

Aesculap Inc.; Aesculap Neurosurgery Pneumatic Kerrison; http://www.aesculapusa.com/assets/base/doc/doc763-pneumatic_kerrison_brochure.pdf; 2008; pp. 12.
Aliaga, Daniel G.; "Image Morphing and Warping", Department of Computer Science; Purdue University; Spring 2010; in 61 pages.
"ARRI Medical Shows SeeFront 3D Display with HD 3D Surgical Microscope", dated Jun. 9, 2013, downloaded from http://www.seefront.com/news-events/article/arri-medical-shows-seefront-3d-display-with-hd-3d-surgical-microscope/.
"Arriscope: A New Era in Surgical Microscopy", Arriscope Brochure published May 20, 2014 in 8 pages.
(Continued)

*Primary Examiner* — Tracy Y Li
(74) *Attorney, Agent, or Firm* — Knobbe, Martens, Olson & Bear LLP

(57) ABSTRACT

A medical apparatus is described for providing visualization of a surgical site. The medical apparatus includes an electronic display disposed within a display housing, the electronic display configured to produce a two-dimensional image. The medical apparatus includes a display optical system disposed within the display housing, the display optical system comprising a plurality of lens elements disposed along an optical path. The display optical system is configured to receive the two-dimensional image from the electronic display, produce a beam with a cross-section that remains substantially constant along the optical path, and produce a collimated beam exiting the opening in the display housing. The medical apparatus can also include an auxiliary video camera configured to provide an oblique view of a patient on the electronic display without requiring a surgeon to adjust their viewing angle through oculars viewing the electronic display.

14 Claims, 20 Drawing Sheets

Related U.S. Application Data filed on Dec. 23, 2013, provisional application No. 61/921,051, filed on Dec. 26, 2013, provisional application No. 61/921,389, filed on Dec. 27, 2013, provisional application No. 61/922,068, filed on Dec. 30, 2013, provisional application No. 61/923,188, filed on Jan. 2, 2014.

(51) Int. Cl.
| | | |
|---|---|---|
| *A61B 1/00* | (2006.01) | |
| *A61B 1/005* | (2006.01) | |
| *A61B 1/05* | (2006.01) | |
| *A61B 1/06* | (2006.01) | |
| *A61B 1/07* | (2006.01) | |
| *A61B 17/02* | (2006.01) | |
| *A61B 17/34* | (2006.01) | |
| *G02B 17/08* | (2006.01) | |
| *G02B 21/00* | (2006.01) | |
| *G02B 21/20* | (2006.01) | |
| *G02B 21/36* | (2006.01) | |
| *G02B 27/02* | (2006.01) | |
| *A61B 90/00* | (2016.01) | |
| *A61B 90/50* | (2016.01) | |
| *A61B 34/20* | (2016.01) | |
| *A61B 90/30* | (2016.01) | |

(52) U.S. Cl.
CPC ............ *A61B 1/051* (2013.01); *A61B 1/0676* (2013.01); *A61B 1/07* (2013.01); *A61B 17/0218* (2013.01); *A61B 17/3423* (2013.01); *A61B 34/20* (2016.02); *A61B 90/361* (2016.02); *A61B 90/50* (2016.02); *G02B 17/08* (2013.01); *G02B 21/0012* (2013.01); *G02B 21/20* (2013.01); *G02B 21/361* (2013.01); *G02B 21/362* (2013.01); *G02B 21/367* (2013.01); *G02B 21/368* (2013.01); *G02B 27/022* (2013.01); *G02B 27/026* (2013.01); *A61B 1/00045* (2013.01); *A61B 2017/3445* (2013.01); *A61B 2034/2057* (2016.02); *A61B 2090/306* (2016.02); *A61B 2090/371* (2016.02)

(56) References Cited

U.S. PATENT DOCUMENTS

| | | |
|---|---|---|
| 3,050,870 A | 8/1962 | Heilig |
| 3,108,781 A | 10/1963 | Saffir |
| 3,128,988 A | 4/1964 | Mandroian |
| 3,141,650 A | 7/1964 | Saffir |
| 3,405,990 A | 10/1968 | Nothnagle et al. |
| 3,409,346 A | 11/1968 | Stapsy |
| 3,664,330 A | 5/1972 | Deutsch |
| 4,056,310 A | 11/1977 | Shimizu et al. |
| 4,063,557 A | 12/1977 | Wuchinich et al. |
| 4,087,198 A | 5/1978 | Theis, Jr. |
| 4,167,302 A | 9/1979 | Karasawa |
| 4,176,453 A | 12/1979 | Abbott |
| 4,223,676 A | 9/1980 | Wuchinich et al. |
| 4,226,228 A | 10/1980 | Shin et al. |
| 4,344,746 A | 8/1982 | Leonard |
| 4,354,734 A | 10/1982 | Nkahashi |
| 4,395,731 A | 7/1983 | Schoolman |
| 4,562,832 A | 1/1986 | Wilder et al. |
| 4,651,201 A | 3/1987 | Schoolman |
| 4,655,557 A | 4/1987 | Takahashi |
| 4,665,391 A | 5/1987 | Spani |
| 4,684,224 A | 8/1987 | Yamashita et al. |
| 4,703,314 A | 10/1987 | Spani |
| 4,750,488 A | 6/1988 | Wuchinich et al. |
| 4,750,902 A | 6/1988 | Wuchinich et al. |
| 4,779,968 A | 10/1988 | Sander |
| 4,783,156 A | 11/1988 | Yokota |
| 4,786,155 A | 11/1988 | Fantone et al. |
| 4,813,927 A | 3/1989 | Morris et al. |
| 4,873,572 A | 10/1989 | Miyazaki et al. |
| 4,900,301 A | 2/1990 | Morris et al. |
| 4,905,670 A | 3/1990 | Adair |
| 4,920,336 A | 4/1990 | Meijer |
| 4,922,902 A | 5/1990 | Wuchinich et al. |
| 4,989,452 A | 2/1991 | Toon et al. |
| 5,032,111 A | 7/1991 | Morris et al. |
| 5,047,009 A | 9/1991 | Morris et al. |
| 5,098,426 A | 3/1992 | Sklar et al. |
| 5,143,054 A | 9/1992 | Adair |
| 5,151,821 A | 9/1992 | Marks |
| 5,176,677 A | 1/1993 | Wuchinich et al. |
| 5,201,325 A | 4/1993 | McEwen et al. |
| 5,221,282 A | 6/1993 | Wuchinich |
| 5,251,613 A | 10/1993 | Adair |
| 5,327,283 A | 7/1994 | Zobel |
| 5,354,314 A | 10/1994 | Hardy et al. |
| 5,417,210 A | 5/1995 | Funda |
| 5,441,059 A | 8/1995 | Dannan |
| 5,464,008 A | 11/1995 | Kim |
| 5,523,810 A | 6/1996 | Volk |
| 5,537,164 A | 7/1996 | Smith |
| 5,553,995 A | 9/1996 | Martinez |
| 5,575,789 A | 11/1996 | Bell et al. |
| 5,584,796 A | 12/1996 | Cohen |
| 5,593,402 A | 1/1997 | Patrick |
| 5,601,549 A | 2/1997 | Miyagi |
| 5,625,493 A | 4/1997 | Matsumura et al. |
| 5,634,790 A | 6/1997 | Pathmanabhan et al. |
| 5,667,481 A | 9/1997 | Villalta et al. |
| 5,697,891 A | 12/1997 | Hori |
| 5,712,995 A | 1/1998 | Cohn |
| 5,716,326 A | 2/1998 | Dannan |
| 5,743,731 A | 4/1998 | Lares et al. |
| 5,743,846 A | 4/1998 | Takahashi et al. |
| 5,747,824 A | 5/1998 | Jung et al. |
| 5,751,341 A | 5/1998 | Chaleki |
| 5,797,403 A | 8/1998 | DiLorenzo |
| 5,803,733 A | 9/1998 | Trott et al. |
| 5,822,036 A | 10/1998 | Massie et al. |
| 5,825,534 A | 10/1998 | Strahle |
| 5,835,266 A | 11/1998 | Kitajima |
| 5,841,510 A | 11/1998 | Roggy |
| 5,861,983 A | 1/1999 | Twisselman |
| 5,889,611 A | 3/1999 | Zonneveld |
| 5,897,491 A | 4/1999 | Kastenbauer et al. |
| 5,909,380 A | 6/1999 | Dubois |
| 5,913,818 A | 6/1999 | Co et al. |
| 5,928,139 A | 7/1999 | Koros et al. |
| 5,949,388 A | 9/1999 | Atsumi |
| 5,982,532 A | 11/1999 | Mittelstadt et al. |
| 6,016,607 A | 1/2000 | Morimoto et al. |
| 6,023,638 A | 2/2000 | Swanson |
| 6,088,154 A | 7/2000 | Morita |
| 6,139,493 A | 10/2000 | Koros et al. |
| 6,152,736 A | 11/2000 | Schmidinger |
| 6,152,871 A | 11/2000 | Foley et al. |
| 6,176,825 B1 | 1/2001 | Chin et al. |
| 6,246,898 B1 | 6/2001 | Vesely et al. |
| 6,293,911 B1 | 9/2001 | Imaizumi et al. |
| 6,317,260 B1 | 11/2001 | Ito |
| 6,319,223 B1 | 11/2001 | Wortrich et al. |
| 6,350,235 B1 | 2/2002 | Cohen et al. |
| 6,354,992 B1 | 3/2002 | Kato |
| 6,398,721 B1 | 6/2002 | Nakamura |
| 6,405,072 B1 | 6/2002 | Cosman |
| 6,434,329 B1 | 8/2002 | Dube et al. |
| 6,443,594 B1 | 9/2002 | Marshall et al. |
| 6,450,706 B1 | 9/2002 | Chapman |
| 6,450,950 B2 | 9/2002 | Irion |
| 6,491,661 B1 | 12/2002 | Boukhny et al. |
| 6,508,759 B1 | 1/2003 | Taylor et al. |
| 6,517,207 B2 | 2/2003 | Chapman |
| 6,525,310 B2 | 2/2003 | Dunfield |
| 6,525,878 B1 | 2/2003 | Takahashi |
| 6,527,704 B1 | 3/2003 | Chang et al. |

(56) References Cited

U.S. PATENT DOCUMENTS

| | | |
|---|---|---|
| 6,538,665 B2 | 3/2003 | Crow et al. |
| 6,549,341 B2 | 4/2003 | Nomura et al. |
| 6,561,999 B1 | 5/2003 | Nazarifar et al. |
| 6,582,358 B2 | 6/2003 | Akui et al. |
| 6,587,711 B1 | 7/2003 | Alfano et al. |
| 6,589,168 B2 | 7/2003 | Thompson |
| 6,618,207 B2 | 9/2003 | Lei |
| 6,626,445 B2 | 9/2003 | Murphy et al. |
| 6,633,328 B1 | 10/2003 | Byrd et al. |
| 6,635,010 B1 | 10/2003 | Lederer |
| 6,636,254 B1 | 10/2003 | Onishi et al. |
| 6,661,571 B1 * | 12/2003 | Shioda ............... A61B 1/04 359/368 |
| 6,668,841 B1 | 12/2003 | Chou |
| 6,698,886 B2 | 3/2004 | Pollack et al. |
| 6,720,988 B1 | 4/2004 | Gere et al. |
| 6,757,021 B1 | 6/2004 | Nguyen-Nhu |
| 6,805,127 B1 | 10/2004 | Karasic |
| 6,824,525 B2 | 11/2004 | Nazarifar et al. |
| 6,847,336 B1 | 1/2005 | Lemelson et al. |
| 6,869,398 B2 | 3/2005 | Obenchain et al. |
| 6,873,867 B2 | 3/2005 | Vilsmeier |
| 6,892,597 B2 | 5/2005 | Tews |
| 6,903,883 B2 | 6/2005 | Amanai |
| 6,908,451 B2 | 6/2005 | Brody et al. |
| 6,985,765 B2 | 1/2006 | Morita |
| 6,996,460 B1 | 2/2006 | Krahnstoever et al. |
| 7,034,983 B2 | 4/2006 | Desimone et al. |
| 7,050,225 B2 | 5/2006 | Nakamura |
| 7,050,245 B2 | 5/2006 | Tesar et al. |
| 7,054,076 B2 | 5/2006 | Tesar et al. |
| 7,116,437 B2 | 10/2006 | Weinstein et al. |
| 7,125,119 B2 | 10/2006 | Farberov |
| 7,150,713 B2 | 12/2006 | Shener et al. |
| 7,150,714 B2 | 12/2006 | Myles |
| 7,154,527 B1 | 12/2006 | Goldstein et al. |
| 7,155,316 B2 | 12/2006 | Sutherland |
| 7,163,543 B2 | 1/2007 | Smedley et al. |
| 7,226,451 B2 | 6/2007 | Shluzas et al. |
| 7,244,240 B2 | 7/2007 | Nazarifar et al. |
| 7,278,092 B2 | 10/2007 | Krzanowski |
| 7,298,393 B2 | 11/2007 | Morita |
| 7,306,559 B2 | 12/2007 | Williams |
| 7,307,799 B2 | 12/2007 | Minefuji |
| 7,326,183 B2 | 2/2008 | Nazarifar et al. |
| 7,471,301 B2 | 12/2008 | Lefevre |
| 7,480,872 B1 | 1/2009 | Ubillos |
| 7,494,463 B2 | 2/2009 | Nehls |
| 7,518,791 B2 | 4/2009 | Sander |
| 7,537,565 B2 | 5/2009 | Bass |
| 7,538,939 B2 | 5/2009 | Zimmerman et al. |
| 7,559,887 B2 | 7/2009 | Dannan |
| 7,633,676 B2 | 12/2009 | Brunner et al. |
| 7,644,889 B2 | 1/2010 | Johnson |
| 7,651,465 B1 | 1/2010 | Sperling et al. |
| 7,713,237 B2 | 5/2010 | Nazarifar et al. |
| 7,764,370 B2 | 7/2010 | Williams et al. |
| 7,766,480 B1 | 8/2010 | Graham et al. |
| 7,777,941 B2 | 8/2010 | Zimmer |
| 7,785,253 B1 | 8/2010 | Arambula |
| 7,786,457 B2 | 8/2010 | Gao |
| 7,806,865 B1 | 10/2010 | Wilson |
| 7,844,320 B2 | 11/2010 | Shahidi |
| 7,872,746 B2 | 1/2011 | Gao et al. |
| 7,874,982 B2 | 1/2011 | Selover |
| 7,896,839 B2 | 3/2011 | Nazarifar et al. |
| 7,907,336 B2 | 3/2011 | Abele et al. |
| 7,927,272 B2 | 4/2011 | Bayer et al. |
| 7,932,925 B2 | 4/2011 | Inbar et al. |
| 7,956,341 B2 | 6/2011 | Gao |
| 8,009,141 B1 | 8/2011 | Chi et al. |
| 8,012,089 B2 | 9/2011 | Bayat |
| 8,018,523 B2 | 9/2011 | Choi |
| 8,018,579 B1 | 9/2011 | Krah |
| 8,027,710 B1 | 9/2011 | Dannan |
| 8,038,612 B2 | 10/2011 | Paz |
| 8,070,290 B2 | 12/2011 | Gille et al. |
| 8,088,066 B2 | 1/2012 | Grey |
| 8,136,779 B2 | 3/2012 | Wilson et al. |
| 8,149,270 B1 | 4/2012 | Yaron et al. |
| 8,159,743 B2 | 4/2012 | Abele et al. |
| 8,169,468 B2 | 5/2012 | Scott et al. |
| 8,187,167 B2 | 5/2012 | Kim |
| 8,187,180 B2 | 5/2012 | Pacey |
| 8,194,121 B2 | 6/2012 | Blumzvig et al. |
| 8,221,304 B2 | 7/2012 | Shioda et al. |
| 8,229,548 B2 | 7/2012 | Frangioni |
| 8,294,733 B2 | 10/2012 | Eino |
| 8,295,693 B2 | 10/2012 | McDowall |
| 8,358,330 B2 | 1/2013 | Riederer |
| 8,405,733 B2 | 3/2013 | Saijo |
| 8,408,772 B2 | 4/2013 | Li |
| 8,409,088 B2 | 4/2013 | Grey et al. |
| 8,419,633 B2 | 4/2013 | Koshikawa et al. |
| 8,419,634 B2 | 4/2013 | Nearmann et al. |
| 8,430,840 B2 | 4/2013 | Nazarifar et al. |
| 8,439,830 B2 | 5/2013 | McKinley et al. |
| 8,460,184 B2 | 6/2013 | Nearman et al. |
| 8,464,177 B2 | 6/2013 | Ben-Yoseph et al. |
| 8,482,606 B2 | 7/2013 | Razzaque |
| 8,498,695 B2 | 7/2013 | Westwick et al. |
| 8,521,331 B2 | 8/2013 | Itkowitz |
| 8,702,602 B2 | 4/2014 | Berci et al. |
| 8,734,328 B2 | 5/2014 | McDowall |
| 8,786,946 B2 | 7/2014 | Nakamura |
| 8,827,899 B2 | 9/2014 | Farr et al. |
| 8,827,902 B2 | 9/2014 | Dietze, Jr. et al. |
| 8,836,723 B2 | 9/2014 | Tsao et al. |
| 8,858,425 B2 | 10/2014 | Farr et al. |
| 8,876,711 B2 | 11/2014 | Lin et al. |
| 8,878,924 B2 | 11/2014 | Farr |
| 8,882,662 B2 | 11/2014 | Charles |
| 8,976,238 B2 | 3/2015 | Ernsperger et al. |
| 8,979,301 B2 | 3/2015 | Moore |
| 9,033,870 B2 | 5/2015 | Farr et al. |
| 9,216,068 B2 | 12/2015 | Tesar |
| 9,492,065 B2 | 11/2016 | Tesar et al. |
| 9,615,728 B2 | 4/2017 | Charles et al. |
| 9,629,523 B2 | 4/2017 | Tesar et al. |
| 9,642,606 B2 | 5/2017 | Charles et al. |
| 9,681,796 B2 | 6/2017 | Tesar et al. |
| 9,723,976 B2 | 8/2017 | Tesar |
| 9,782,159 B2 | 10/2017 | Tesar |
| 2001/0055062 A1 | 12/2001 | Shioda et al. |
| 2002/0013514 A1 | 1/2002 | Brau |
| 2002/0049367 A1 | 4/2002 | Irion et al. |
| 2002/0065461 A1 | 5/2002 | Cosman |
| 2002/0082498 A1 | 6/2002 | Wendt et al. |
| 2003/0055410 A1 | 3/2003 | Evans et al. |
| 2003/0059097 A1 | 3/2003 | Abovitz et al. |
| 2003/0078494 A1 | 4/2003 | Panescu et al. |
| 2003/0088179 A1 | 5/2003 | Seeley et al. |
| 2003/0103191 A1 | 6/2003 | Staurenghi et al. |
| 2004/0017607 A1 | 1/2004 | Hauger et al. |
| 2004/0036962 A1 | 2/2004 | Brunner et al. |
| 2004/0070822 A1 | 4/2004 | Shioda et al. |
| 2004/0087833 A1 | 5/2004 | Bauer et al. |
| 2004/0111183 A1 | 6/2004 | Sutherland |
| 2004/0196553 A1 | 10/2004 | Banju et al. |
| 2004/0230191 A1 | 11/2004 | Frey et al. |
| 2005/0018280 A1 | 1/2005 | Richardson |
| 2005/0019722 A1 | 1/2005 | Schmid et al. |
| 2005/0026104 A1 | 2/2005 | Takahashi |
| 2005/0063047 A1 | 3/2005 | Obrebski et al. |
| 2005/0064936 A1 | 3/2005 | Pryor |
| 2005/0065435 A1 | 3/2005 | Rauch et al. |
| 2005/0095554 A1 | 5/2005 | Wilkinson |
| 2005/0107808 A1 | 5/2005 | Evans et al. |
| 2005/0215866 A1 | 9/2005 | Kim |
| 2005/0228232 A1 | 10/2005 | Gillinov et al. |
| 2005/0279355 A1 | 12/2005 | Loubser |
| 2006/0004261 A1 | 1/2006 | Douglas |
| 2006/0020213 A1 | 1/2006 | Whitman et al. |
| 2006/0025656 A1 | 2/2006 | Buckner et al. |

(56) References Cited

U.S. PATENT DOCUMENTS

| | | |
|---|---|---|
| 2006/0069315 A1 | 3/2006 | Miles et al. |
| 2006/0069316 A1 | 3/2006 | Dorfman et al. |
| 2006/0085969 A1 | 4/2006 | Bennett et al. |
| 2006/0092178 A1 | 5/2006 | Tanguya, Jr. et al. |
| 2006/0114411 A1 | 6/2006 | Wei et al. |
| 2006/0129140 A1 | 6/2006 | Todd et al. |
| 2006/0152516 A1 | 7/2006 | Plummer |
| 2006/0235279 A1 | 10/2006 | Hawkes et al. |
| 2006/0236264 A1 | 10/2006 | Cain et al. |
| 2006/0241499 A1 | 10/2006 | Irion et al. |
| 2006/0276693 A1 | 12/2006 | Pacey |
| 2006/0293557 A1 | 12/2006 | Chuanggui et al. |
| 2007/0010716 A1 | 1/2007 | Malandain |
| 2007/0019916 A1 | 1/2007 | Takami |
| 2007/0038080 A1 | 2/2007 | Salisbury, Jr. et al. |
| 2007/0086205 A1 | 4/2007 | Krupa et al. |
| 2007/0153541 A1 | 7/2007 | Bennett et al. |
| 2007/0173853 A1 | 7/2007 | MacMillan |
| 2007/0238932 A1 | 10/2007 | Jones et al. |
| 2007/0282171 A1 | 12/2007 | Karpowicz et al. |
| 2008/0015417 A1 | 1/2008 | Hawkes et al. |
| 2008/0058606 A1 | 3/2008 | Miles et al. |
| 2008/0081947 A1 | 4/2008 | Irion et al. |
| 2008/0091066 A1 | 4/2008 | Sholev |
| 2008/0096165 A1 | 4/2008 | Virnicchi et al. |
| 2008/0097467 A1 | 4/2008 | Gruber et al. |
| 2008/0151041 A1 | 6/2008 | Shafer et al. |
| 2008/0183038 A1 | 7/2008 | Tilson et al. |
| 2008/0195128 A1 | 8/2008 | Orbay et al. |
| 2008/0221394 A1 | 9/2008 | Melkent et al. |
| 2008/0221591 A1 | 9/2008 | Farritor et al. |
| 2008/0266840 A1 | 10/2008 | Nordmeyer et al. |
| 2008/0269564 A1 | 10/2008 | Gelnett |
| 2008/0278571 A1 | 11/2008 | Mora |
| 2008/0300465 A1 | 12/2008 | Feigenwinter et al. |
| 2008/0303899 A1 | 12/2008 | Berci |
| 2008/0319266 A1 | 12/2008 | Poll et al. |
| 2009/0030436 A1 | 1/2009 | Charles |
| 2009/0034286 A1 | 2/2009 | Krupa et al. |
| 2009/0040783 A1 | 2/2009 | Krupa et al. |
| 2009/0105543 A1 | 4/2009 | Miller et al. |
| 2009/0137893 A1 | 5/2009 | Seibel et al. |
| 2009/0137989 A1 | 5/2009 | Kataoka |
| 2009/0149716 A1 | 6/2009 | Diao et al. |
| 2009/0156902 A1 | 6/2009 | Dewey et al. |
| 2009/0185392 A1 | 7/2009 | Krupa et al. |
| 2009/0190209 A1 | 7/2009 | Nakamura |
| 2009/0190371 A1 | 7/2009 | Root et al. |
| 2009/0209826 A1 | 8/2009 | Sanders et al. |
| 2009/0244259 A1 | 10/2009 | Kojima et al. |
| 2009/0245600 A1 | 10/2009 | Hoffman et al. |
| 2009/0248036 A1 | 10/2009 | Hoffman et al. |
| 2009/0258638 A1 | 10/2009 | Lee |
| 2009/0304582 A1 | 12/2009 | Rousso et al. |
| 2009/0318756 A1 | 12/2009 | Fisher et al. |
| 2009/0326322 A1 | 12/2009 | Diolaiti |
| 2009/0326331 A1 | 12/2009 | Rosen |
| 2010/0013910 A1 | 1/2010 | Farr |
| 2010/0013971 A1 | 1/2010 | Amano |
| 2010/0107118 A1 | 4/2010 | Pearce |
| 2010/0128350 A1 | 5/2010 | Findlay et al. |
| 2010/0168520 A1 | 7/2010 | Poll et al. |
| 2010/0182340 A1 | 7/2010 | Bachelder et al. |
| 2010/0198014 A1 | 8/2010 | Poll et al. |
| 2010/0198241 A1 | 8/2010 | Gerrah et al. |
| 2010/0208046 A1 | 8/2010 | Takahashi |
| 2010/0245557 A1 | 9/2010 | Luley, III et al. |
| 2010/0249496 A1 | 9/2010 | Cardenas et al. |
| 2010/0286473 A1 | 11/2010 | Roberts |
| 2010/0305409 A1 | 12/2010 | Chang |
| 2010/0312069 A1 | 12/2010 | Sutherland et al. |
| 2010/0318099 A1 | 12/2010 | Itkowitz et al. |
| 2010/0331855 A1 | 12/2010 | Zhao et al. |
| 2011/0034781 A1 | 2/2011 | Loftus |
| 2011/0038040 A1 | 2/2011 | Abele et al. |
| 2011/0063734 A1 | 3/2011 | Sakaki |
| 2011/0065999 A1 | 3/2011 | Manzanares |
| 2011/0071359 A1 | 3/2011 | Bonadio et al. |
| 2011/0080536 A1 | 4/2011 | Nakamura et al. |
| 2011/0115882 A1 | 5/2011 | Shahinian et al. |
| 2011/0144436 A1 | 6/2011 | Nearman et al. |
| 2011/0178395 A1 | 7/2011 | Miesner et al. |
| 2011/0184243 A1 | 7/2011 | Wright et al. |
| 2011/0190588 A1 | 8/2011 | McKay |
| 2011/0234841 A1 | 9/2011 | Akeley et al. |
| 2011/0249323 A1 | 10/2011 | Tesar et al. |
| 2011/0257488 A1 | 10/2011 | Koyama et al. |
| 2011/0263938 A1 | 10/2011 | Levy |
| 2011/0264078 A1 | 10/2011 | Lipow et al. |
| 2011/0288560 A1 | 11/2011 | Shohat et al. |
| 2011/0298704 A1 | 12/2011 | Krah |
| 2011/0301421 A1 | 12/2011 | Michaeli et al. |
| 2011/0316994 A1 | 12/2011 | Lemchen |
| 2012/0029280 A1 | 2/2012 | Kucklick |
| 2012/0035423 A1 | 2/2012 | Sebastian et al. |
| 2012/0035638 A1 | 2/2012 | Mathaneswaran et al. |
| 2012/0040305 A1 | 2/2012 | Karazivan et al. |
| 2012/0041272 A1 | 2/2012 | Dietze, Jr. et al. |
| 2012/0059222 A1 | 3/2012 | Yoshida |
| 2012/0065468 A1 | 3/2012 | Levy et al. |
| 2012/0087006 A1 | 4/2012 | Signaigo |
| 2012/0088974 A1 | 4/2012 | Maurice |
| 2012/0097567 A1 | 4/2012 | Zhao et al. |
| 2012/0108900 A1 | 5/2012 | Viola et al. |
| 2012/0116173 A1 | 5/2012 | Viola |
| 2012/0127573 A1 | 5/2012 | Robinson et al. |
| 2012/0130399 A1 | 5/2012 | Moll et al. |
| 2012/0134028 A1 | 5/2012 | Maruyama |
| 2012/0157787 A1 | 6/2012 | Weinstein et al. |
| 2012/0157788 A1 | 6/2012 | Serowski et al. |
| 2012/0158015 A1 | 6/2012 | Fowler et al. |
| 2012/0190925 A1 | 7/2012 | Luiken |
| 2012/0197084 A1 | 8/2012 | Drach et al. |
| 2012/0230668 A1 | 9/2012 | Vogt |
| 2012/0232352 A1 | 9/2012 | Lin et al. |
| 2012/0245432 A1 | 9/2012 | Karpowicz et al. |
| 2012/0265023 A1 | 10/2012 | Berci et al. |
| 2012/0320102 A1 | 12/2012 | Jorgensen |
| 2012/0330129 A1* | 12/2012 | Awdeh ................ A61B 5/7425 600/411 |
| 2013/0012770 A1 | 1/2013 | Su |
| 2013/0027516 A1 | 1/2013 | Hart et al. |
| 2013/0041226 A1 | 2/2013 | McDowall |
| 2013/0041368 A1 | 2/2013 | Cunningham et al. |
| 2013/0060095 A1 | 3/2013 | Bouquet |
| 2013/0066304 A1 | 3/2013 | Belson et al. |
| 2013/0072917 A1 | 3/2013 | Kaschke et al. |
| 2013/0077048 A1* | 3/2013 | Mirlay ................ A61B 3/145 351/206 |
| 2013/0085337 A1 | 4/2013 | Hess et al. |
| 2013/0197313 A1 | 8/2013 | Wan |
| 2013/0245383 A1 | 9/2013 | Friedrich et al. |
| 2013/0331730 A1 | 12/2013 | Fenech et al. |
| 2014/0005485 A1 | 1/2014 | Tesar et al. |
| 2014/0005486 A1 | 1/2014 | Charles |
| 2014/0005487 A1 | 1/2014 | Tesar |
| 2014/0005488 A1 | 1/2014 | Charles et al. |
| 2014/0005489 A1 | 1/2014 | Charles |
| 2014/0005555 A1 | 1/2014 | Tesar |
| 2014/0081659 A1 | 3/2014 | Nawana et al. |
| 2014/0168799 A1 | 6/2014 | Hurbert et al. |
| 2014/0179998 A1 | 6/2014 | Pacey et al. |
| 2014/0187859 A1 | 7/2014 | Leeuw et al. |
| 2014/0198190 A1 | 7/2014 | Okumu |
| 2014/0247482 A1 | 9/2014 | Doi et al. |
| 2014/0275801 A1 | 9/2014 | Menchaca et al. |
| 2014/0276008 A1 | 9/2014 | Steinbach et al. |
| 2014/0285403 A1 | 9/2014 | Kobayashi |
| 2014/0316209 A1 | 10/2014 | Overes et al. |
| 2014/0347395 A1 | 11/2014 | Tsao et al. |
| 2014/0378843 A1 | 12/2014 | Valdes et al. |
| 2015/0018622 A1 | 1/2015 | Tesar |
| 2015/0025324 A1 | 1/2015 | Wan |
| 2015/0087918 A1 | 3/2015 | Vasan |

(56) References Cited

U.S. PATENT DOCUMENTS

| | | | |
|---|---|---|---|
| 2015/0094533 | A1 | 4/2015 | Kleiner et al. |
| 2015/0112148 | A1 | 4/2015 | Bouquet |
| 2015/0141755 | A1 | 5/2015 | Tesar |
| 2015/0238073 | A1 | 8/2015 | Charles |
| 2015/0297311 | A1 | 10/2015 | Tesar |
| 2016/0220324 | A1 | 8/2016 | Tesar |
| 2017/0020627 | A1 | 1/2017 | Tesar |
| 2017/0143442 | A1 | 5/2017 | Tesar |

FOREIGN PATENT DOCUMENTS

| | | |
|---|---|---|
| CN | 102495463 | 6/2012 |
| CN | 202920720 | 11/2012 |
| DE | 103 41 125 | 4/2005 |
| DE | 10 2010 030 2 | 12/2011 |
| EP | 0 233 940 | 11/1993 |
| EP | 0 466 705 | 6/1996 |
| EP | 1 175 106 | 1/2002 |
| EP | 1 333 305 | 8/2003 |
| EP | 2 641 561 | 9/2013 |
| JP | 07-261094 | 10/1995 |
| JP | 08-131399 | 5/1996 |
| JP | 2001-117049 | 4/2001 |
| JP | 3402797 | 5/2003 |
| JP | 2003-322803 | 11/2003 |
| JP | 2004-024835 | 1/2004 |
| JP | 3549253 | 8/2004 |
| JP | 2007-068876 | 3/2007 |
| JP | 4503748 | 7/2010 |
| JP | 2010-206495 | 9/2010 |
| JP | 2011-118741 | 6/2011 |
| WO | WO 87/001276 | 3/1987 |
| WO | WO 91/012034 | 8/1991 |
| WO | WO 99/17661 | 4/1999 |
| WO | WO 00/078372 | 12/2000 |
| WO | WO 01/072209 | 10/2001 |
| WO | WO 2008/073243 | 6/2008 |
| WO | WO 2010/079817 | 7/2010 |
| WO | WO 2010/114843 | 10/2010 |
| WO | WO 2010/123578 | 10/2010 |
| WO | WO 2011/069469 | 6/2011 |
| WO | WO 2012/047962 | 4/2012 |
| WO | WO 2012/078989 | 6/2012 |
| WO | WO 2013/049679 | 4/2013 |
| WO | WO 2013/109966 | 7/2013 |
| WO | WO 2013/116489 | 8/2013 |
| WO | WO 2014/004717 | 1/2014 |
| WO | WO 2014/060412 | 4/2014 |
| WO | WO 2014/189969 | 11/2014 |
| WO | WO 2015/042460 | 3/2015 |
| WO | WO 2015/042483 | 3/2015 |
| WO | WO 2015/100310 | 7/2015 |
| WO | WO 2016/090336 | 6/2016 |
| WO | WO 2016/154589 | 9/2016 |
| WO | WO 2017/091704 | 6/2017 |

OTHER PUBLICATIONS

AustriaMicroSystems; "AS5050: Smallest Magnetic Rotary Encoder for μA Low Power Applications"; www.austriamicrosystems.com/AS5050 printed Nov. 2012 in 2 pages.
Bayonet Lock Video, 00:16 in length, Date Unknown, Received Oct. 15, 2014 [Screenshots captured at 00:00, 00:02, 00:05, 00:08, and 00:16].
BellowsTech; "Actuators"; www.bellowstech.com/metal-bellows/actuators/ printed Jul. 17, 2012 in 4 pages.
"Carl Zeiss Unveils $99 VR One Virtual Reality Headset"; www.electronista.com/articles/14/10/10/zeiss.vr.one.able.to.accept.variety.of.smartphones.using.custom.trays printed Oct. 13, 2014 in 2 pages.
Designboom; "Bright LED"; http://www.designboom.com/project/fiber-optics-light-glove/; Sep. 28, 2007.
FEI-FEI, Li; Lecture 10: Multi-View Geometry; Stanford Vision Lab; Oct. 24, 2011; pp. 89.
"Fuse™. Full Spectrum Endoscopy™"; http://www.endochoice.com/Fuse printed Oct. 7, 2013 in 3 pages.
Hardesty, Larry; "3-D Cameras for Cellphones: Clever math could enable a high-quality 3-D camera so simple, cheap and power-efficient that it could be incorporated into handheld devices"; MIT News Office; http://web.mit.edu/newsoffice/2011/lidar-3d-camera-cellphones-0105.html; Jan. 5, 2012; pp. 4.
Hartley et al.; "Multiple View Geometry in Computer Vision: Chapter 9—Epipolar Geometry and the Fundamental Matrix"; http://www.robots.ox.ac.uk/~vgg/hzbook/hzbook2/HZepipolar.pdf; Mar. 2004; 2nd Edition; Ch. 9; pp. 239-261.
Heidelberg Engineering; "MultiColor: Scanning Laser Imaging"; http://www.heidelbergengineering.com/us/products/spectralis-models/imaging-modes/multicolor/; Copyright © 2013; printed Apr. 5, 2013.
Krishna, Golden; "Watch: What Good is a Screen?" http://www.cooper.com/author/golden_krishna as printed Jul. 9, 2014 in 62 pages.
Lang et al.; "ZEISS Microscopes for Microsurgery"; Springer-Verlag; Berlin, Heidelberg; 1981.
Leica Micrsosystems, "Images TrueVision Integrated 3D," http://www.leica-microsystems.com/products/surgical-microscopes/neurosurgery-spine/details/product/truevision-integrated-3d/gallery/, Nov. 26, 2014, pp. 3.
Leica Micrsosystems, "Leica Microsystems' Ophthalmic Surgical Microscopes with TrueVision 3D Technology Available Globally," http://www.leica-microsystems.com/products/surgical-microscopes/neurosurgery-spine/details/product/truevision-integrated-3d/news/, Sep. 18, 2014, pp. 5.
Male Bayonet Video, 00:04 in length, Date Unknown, Received Oct. 10, 2014 [Screenshots captured at 00:00, 00:01, 00:02, 00:03, and 00:04].
Melexis; "MLX75031 Optical Gesture and Proximity Sensing IC"; http://melexis.com/optical-sensors/optical-sensing.mlx75031-815.aspx?sta printed Mar. 15, 2013 in 1 page.
MMR Technologies; "Micro Miniature Refrigerators"; www.mmr-tech.com/mmr_overview.php; Copyright © 2011; printed Feb. 11, 2013.
Moog; "Surgical Handpieces: Therapeutic Ultrasonic Devices"; http://www.moog.com/products/surgical-hpieces/ printed Sep. 25, 2013 in 1 page.
Morita; "TwinPower Turbine® High Speed Handpieces Standard, 45° ., and Ultra Series Head Designs"; J. Morita Mfg. Corp., http://www.morita.com/usa/root/img/pool/pdf/product_brochures/twinpower_brochure_1-264_0512_web.pdf; May 2012; pp. 20.
Olympus; "Olympus Introduces the World's First and Only Monopolar, Disposable Tonsil Adenoid Debrider (DTAD)"; http://www.olympusamerica.com/corporate/corp_presscenter_headline.asp?pressNo=926; Sep. 11, 2012; pp. 2.
OmniVision; "OV2722 full HD (1080p) product brief: 1/6-Inch Native 1080p HD CameraChip Sensor for Ultra-Compact Applications"; http://web.archive.org/web/20120730043057/http://www.ovt.com/download_document.php?type=sensor&sensorid=119; May 2012 in 2 pages.
Orthofix; "ProView MAP System Retractors"; www.us.orthofix.com/products/proviewretractors.asp?cid=39; Copyright © 2010; printed Apr. 1, 2013.
OrtusTech; "Sample Shipment Start: World's Smallest Size Full-HD Color TFT LCD"; http://ortustech.co.jp/english/notice/20120427.html printed May 22, 2012 in 2 pages.
SAAB, Mark; "Applications of High-Pressure Balloons in the Medical Device Industry"; http://www.ventionmedical.com/documents/medicalballoonpaper.pdf; Copyright © 1999; pp. 19.
Purcher, Jack, "Apple Wins a Patent for an Oculus Rift-Like Display System," http://www.patentlyapple.com/patently-apple/2014/09/apple-wins-a-patent-for-an-oculus-rift-like-display-system.html, Sep. 9, 2014.
Savage, Lynn; "Sound and Light, Signifying Improved Imaging"; www.photonics.com/Article.aspx?AID=45039; Nov. 1, 2010; pp. 6.
Timm, Karl Walter; "Real-Time View Morphing of Video Streams"; University of Illinois; Chicago, Illinois; 2003; pp. 168.

(56) References Cited

OTHER PUBLICATIONS

TrueVision Microscopes, http://truevisionmicroscopes.com/images/productsnew/081a-f.jpg, printed Nov. 26, 2014 in 1 page.
TrueVision, "About TrueVision," http://web.archive.org/web/20071208125103/http://www.truevisionsys.com/about.html, as viewed Dec. 8, 2007 in 2 pages.
TrueVision "Leica Microsystems and TrueVision® 3D Surgical create the first 3D digital hybrid microscope", Press Release, Oct. 5, 2012, pp. 2.
TrueVision, "TrueVision Technology," http://web.archive.org/web/20071208125125/http://www.truevisionsys.com/technology.html, as viewed Dec. 8, 2007 in 2 pages.
Whitney et al.; "Pop-up book MEMS"; Journal of Micromechanics and Microengineering; Oct. 14, 2011; vol. 21; No. 115021; pp. 7.
Wikipedia, "Zoom Lens," http://en.wikipedia.org/wiki/Optical_Zoom, printed Oct. 7, 2014 in 3 pages.
Zeiss; "Informed for Medical Professionals, Focus: Fluorescence"; Carl Zeiss; 2nd Issue; Oct. 2006; 30-801-LBW-GFH-X-2006; Printed in Germany; pp. 32.
Zeiss; "Ophthalmic Surgery in Its Highest Form, OPMI® VISU 210"; Carl Zeiss, 2005, 30-097/III-e/USA Printed in Germany AW-TS-V/2005 Uoo; pp. 19.
Zeiss; "SteREO Discovery. V12, Expanding the Boundaries"; Carl Zeiss, Sep. 2004; 46-0008 e 09.2004, pp. 6.
Zeiss, "Stereomicroscopes: Stemi SV 6, SV 11, SV 11 Apo," The Profile, pp. 30.
Zeiss; "Time for a Change: OPMI® pico for ENT"; Carl Zeiss, 2005, 30-451/III-e Printed in Germany LBW-TS-V/2005 Uoo, pp. 8.
Zhang, Michael; "LIFX: A WiFi-Enabled LED Bulb that May Revolutionize Photographic Lighting"; http://www.petapixel.com/2012/09/22/lifx-a-wifi-enabled-led-bulb-that-may-revolutionize-photographic-lighting/ printed Sep. 28, 2012 in 9 pages.
Restriction Requirement in U.S. Appl. No. 13/802,362, dated Oct. 23, 2013.
Office Action in U.S. Appl. No. 13/802,362, dated Dec. 17, 2013.
Office Action in U.S. Appl. No. 13/802,362, dated Apr. 7, 2014.
Office Action in U.S. Appl. No. 13/802,362, dated Jan. 27, 2015.
International Search Report and Written Opinion in PCT Application No. PCT/US2013/047972, dated Jan. 3, 2014.
Office Action in U.S. Appl. No. 13/802,162, dated Feb. 12, 2015.
Office Action in U.S. Appl. No. 13/802,485, dated Jun. 20, 2014.
Restriction Requirement in U.S. Appl. No. 13/802,635, dated May 28, 2014.
Office Action in U.S. Appl. No. 13/802,509, dated Sep. 9, 2013.
Notice of Allowance in U.S. Appl. No. 13/802,509, dated Apr. 16, 2014.
Restriction Requirement in U.S. Appl. No. 13/802,582, dated Oct. 23, 2013.
Office Action in U.S. Appl. No. 13/802,582, dated Dec. 16, 2013.
Office Action in U.S. Appl. No. 13/802,582, dated Apr. 16, 2014.
Office Action in U.S. Appl. No. 13/802,582, dated Jan. 29, 2015.
International Search Report and Written Opinion in PCT Application No. PCT/US2014/038839, dated Oct. 17, 2014.
International Search Report and Written Opinion in PCT Application No. PCT/US2014/056643, dated Dec. 11, 2014.
Invitation to Pay Additional Fees in PCT Application No. PCT/US2014/056681, dated Jan. 14, 2015.
Kramer, Jennifer; "The Right Filter Set Gets the Most out of a Microscope"; Biophotonics International; Jan./Feb. 1999; vol. 6; pp. 54-58.
Lutze et al.; "Microsystems Technology for Use in a Minimally Invasive Endoscope Assisted Neurosurgical Operating System—MINOP II"; 2005; http://web.archive.org/web/20151120215151/http://www.meditec.hia.rwth-aachen.de/fileadmin/content/meditec/bilder/forschung/aktuelle_projekte/robotische/Exoscope_Aesculap.pdf; Nov. 20, 2015 in 4 pages.
MediTec; "MINOP II—Robotical Microscope Platform"; http://web.archive.org/web/20151120213932/http://www.meditec.hia.rwth-aachen.de/en/research/former-project/minop-II/; Nov. 20, 2015 in 3 pages.
"Narrow Band Imaging"; http://web.archive.org/web/20150701233623/https://en.wikipedia.org/wiki/Narrow_band_imaging printed Jul. 1, 2015 in 1 page.
Rustum, Dr. Abu; "ICG Mapping Endometrial Cancer"; Pinpoint Endometrium Ca Lenfedenektomi MSKCC May 2013; Memorial Sloan Kettering Cancer Center; May 2013; Published to YouTube.com Sep. 1, 2013; in 2 pages; http://web.archive.org/web/20150402210857/https://www.youtube.com/watch?v=DhChvaUCe4I.
Sun et al.; "Neurotoxin-Directed Synthesis and in Vitro Evaluation of Au Nanoclusters"; RSC Advances, 2015; vol. 5, No. 38; pp. 29647-29652.
Zhang, Sarah; "The Obscure Neuroscience Problem That's Plaguing VR"; http://web.archive.org/web/20150812172934/http://www.wired.com/2015/08/obscure-neuroscience-problem-thats-plaguing-vr/; Aug. 11, 2015 in 5 pages.
Preliminary Amendment in U.S. Appl. No. 14/411,068, dated Aug. 13, 2015.
Office Action in U.S. Appl. No. 14/411,068, dated Aug. 17, 2017.
Official Communication in European Application No. 13808996.6, dated Jan. 4, 2016.
Official Communication in European Application No. 13808996.6, dated Apr. 14, 2016.
Official Communication in European Application No. 13808996.6, dated Feb. 21, 2017.
Official Communication in European Application No. 13808996.6, dated Jun. 6, 2017.
Official Communication in Japanese Application No. 2015-520471, dated May 9, 2017.
Official Communication in Japanese Application No. 2015-520471, dated Nov. 21, 2017.
International Preliminary Report on Patentability in PCT Application No. PCT/US2013/047972, dated Jan. 8, 2015.
Office Action in U.S. Appl. No. 13/802,635, dated Mar. 27, 2015.
Final Office Action in U.S. Appl. No. 13/802,635, dated Jan. 14, 2016.
Response to Final Office Action in U.S. Appl. No. 13/802,635, dated Jul. 13, 2016.
Office Action in U.S. Appl. No. 13/802,635, dated Sep. 27, 2016.
Amendment and Response to Office Action in U.S. Appl. No. 13/802,635, dated Mar. 24, 2017.
Notice of Allowance in U.S. Appl. No. 13/802,635, dated Apr. 27, 2017.
Notice of Allowance in U.S. Appl. No. 13/802,635, dated Aug. 15, 2017.
Amendment in U.S. Appl. No. 15/589058, dated Nov. 15, 2017.
Office Action in U.S. Appl. No. 15/589058, dated Dec. 8, 2017.
Office Action in U.S. Appl. No. 13/802,577, dated Sep. 30, 2016.
Response to Office Action in U.S. Appl. No. 13/802,577, dated Mar. 29, 2017.
Notice of Allowance in U.S. Appl. No. 13/802,577, dated Apr. 24, 2017.
Amendment in U.S. Appl. No. 13/802,577, dated May 25, 2017.
Office Action in U.S. Appl. No. 13/802,577, dated Jun. 20, 2017.
Amendment in U.S. Appl. No. 13/802,577, dated Nov. 20, 2017.
Notice of Allowance in U.S. Appl. No. 13/802,577, dated Dec. 6, 2017.
Official Communication in European Application No. 14800423.7, dated Feb. 8, 2017.
International Preliminary Report on Patentability in PCT Application No. PCT/US2014/038839, dated Dec. 3, 2015.
Preliminary Amendment in U.S. Appl. No. 14/491,935, dated Feb. 5, 2015.
Restriction Requirement in U.S. Appl. No. 14/491,935, dated Sep. 8, 2017.
Partial Supplementary European Search Report in European Application No. 14845427.5, dated May 4, 2017.
Extended European Search Report in European Application No. 14845427.5, dated Aug. 8, 2017.

(56) References Cited

OTHER PUBLICATIONS

European Search Report in European Application No. 14846410.0, dated Jun. 23, 2017.
International Preliminary Report on Patentability and Written Opinion in PCT Application No. PCT/US2014/056643, dated Mar. 31, 2016.
International Search Report and Written Opinion in PCT Application No. PCT/US2014/056681, dated Mar. 20, 2015.
International Preliminary Report on Patentability and Written Opinion in PCT Application No. PCT/US2014/056681, dated Mar. 31, 2016.
Preliminary Amendment in U.S. Appl. No. 14/581,779, dated Jul. 6, 2015.
Restriction Requirement in U.S. Appl. No. 14/581,779, dated Oct. 31, 2017.
Extended European Search Report in European Application No. 14873324.9, dated 25, 2017.
Invitation to Pay Additional Fees in PCT Application No. PCT/US2014/072121, dated Mar. 2, 2015.
International Search Report and Written Opinion in PCT Application No. PCT/US2014/072121, dated May 1, 2015.
International Preliminary Report on Patentability and Written Opinion in PCT Application No. PCT/US2014/072121, dated Jul. 7, 2016.
Preliminary Amendment in U.S. Appl. No. 14/960,276, dated Apr. 18, 2016.
Office Action in U.S. Appl. No. 14/960,276, dated Jul. 28, 2017.
International Search Report and Written Opinion in PCT Application No. PCT/US2015/064133, dated Feb. 9, 2016.
International Preliminary Report on Patentability and Written Opinion in PCT Application No. PCT/US2015/064133, dated Jun. 15, 2017.
Preliminary Amendment in U.S. Appl. No. 15/081,653, dated Oct. 11, 2016.
International Search Report and Written Opinion in PCT Application No. PCT/US2016/024330, dated Jul. 1, 2016.
International Preliminary Report on Patentability and Written Opinion in PCT Application No. PCT/US2016/024330, dated Oct. 5, 2017.
Preliminary Amendment in U.S. Appl. No. 15/360,565, dated Feb. 6, 2017.
Invitation to Pay Additional Fees in PCT Application No. PCT/US2016/063549, dated Feb. 2, 2017.
International Search Report and Written Opinion in PCT Application No. PCT/US2016/063549, dated Apr. 14, 2017.

\* cited by examiner

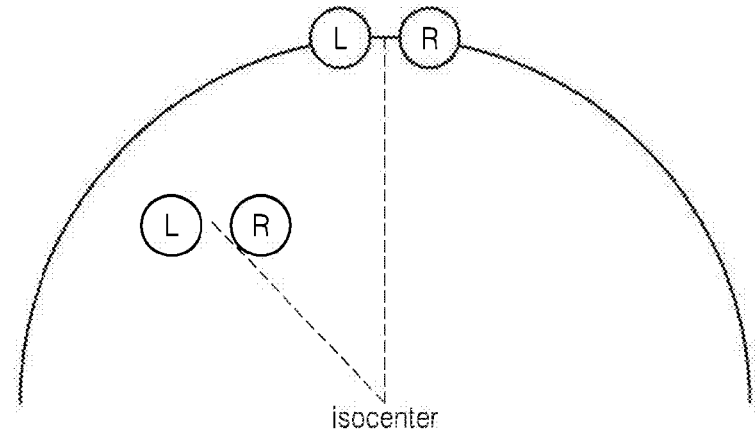
The display provides a horizon consistent with an ergonomically advantageous viewing position for the user. The isocenter is defined as the postion bewtween the two eyes parallel to the display's horizon.
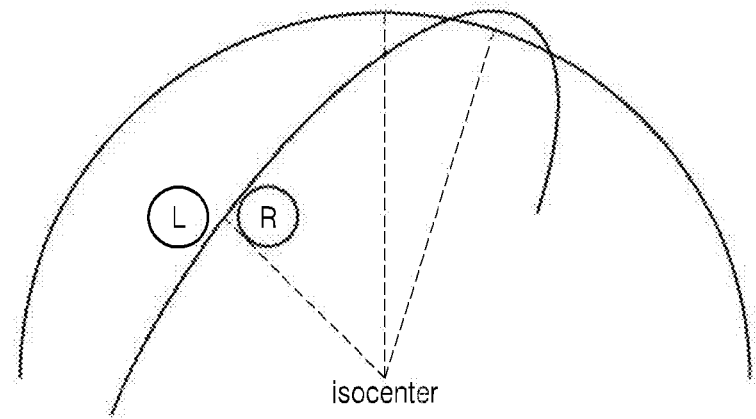
FIG. 3B

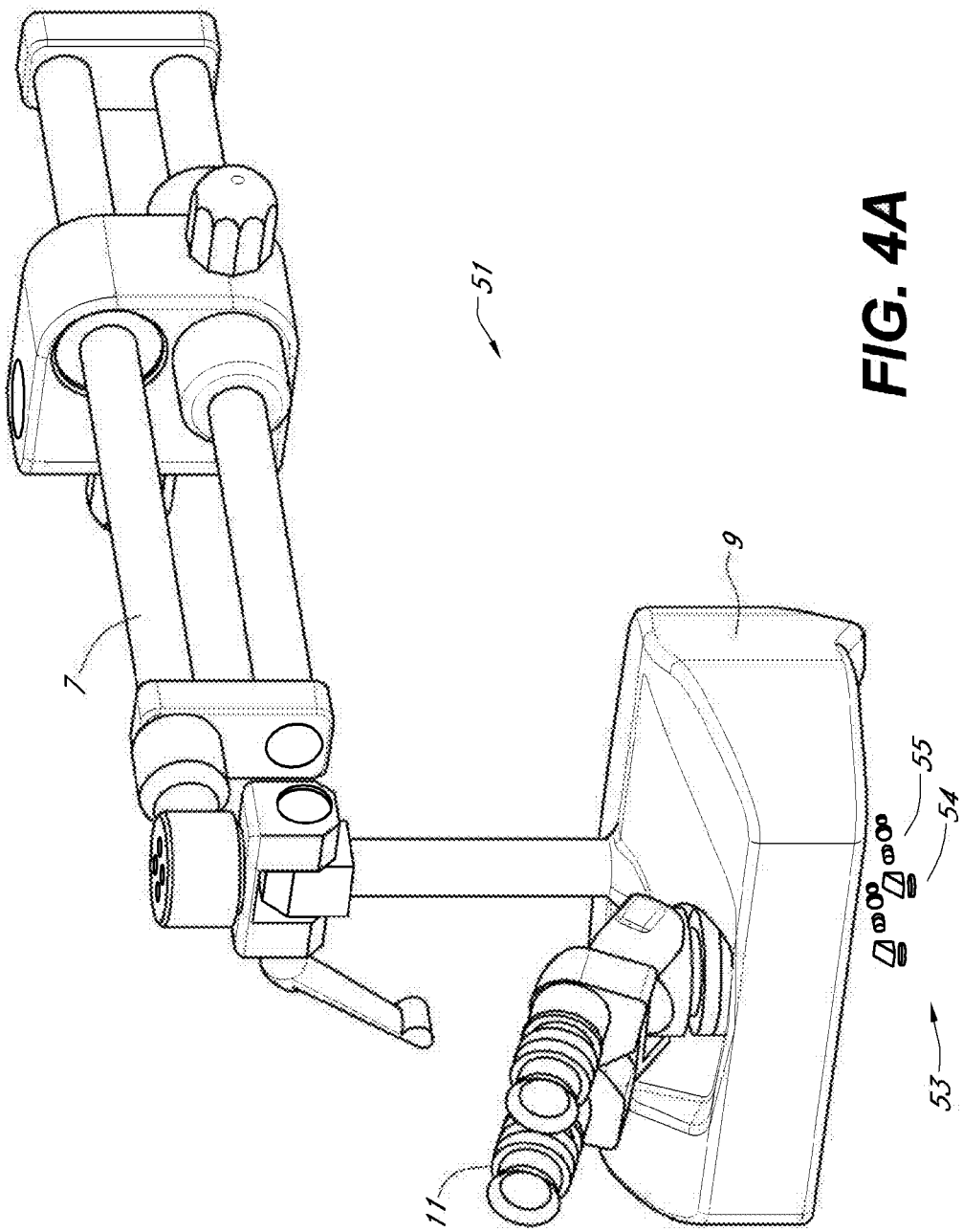

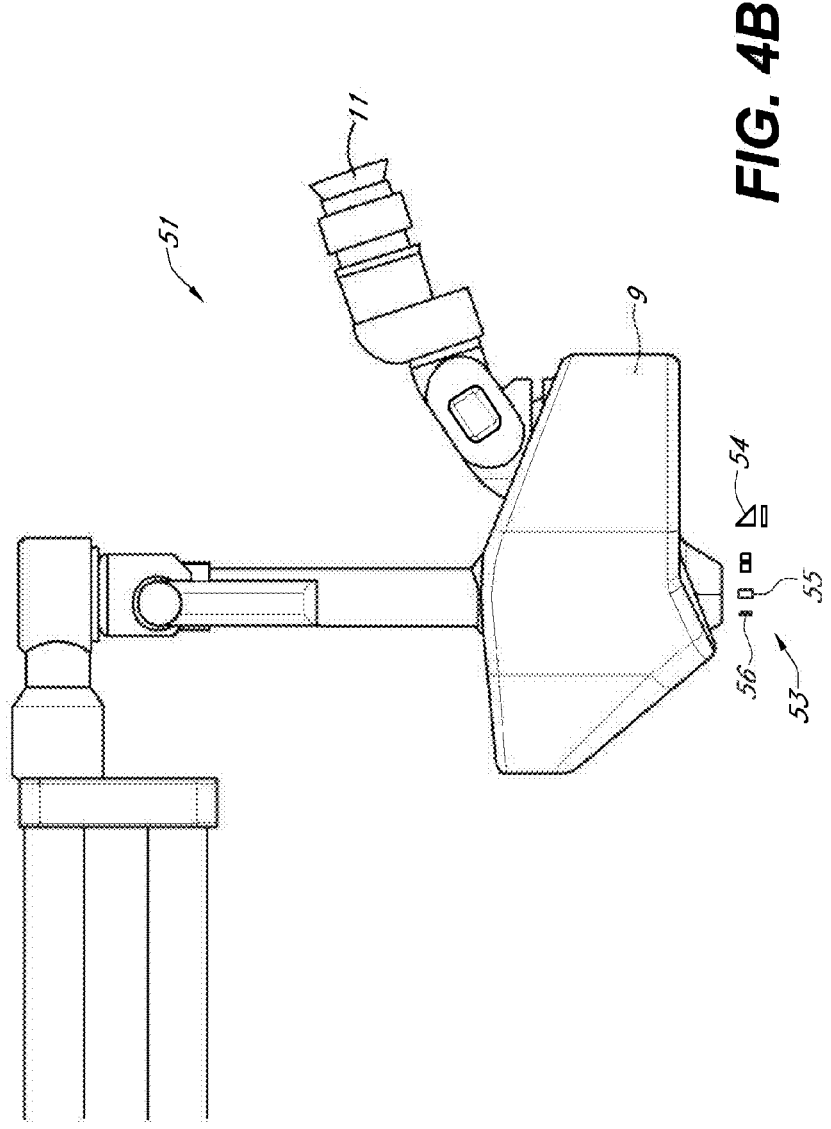

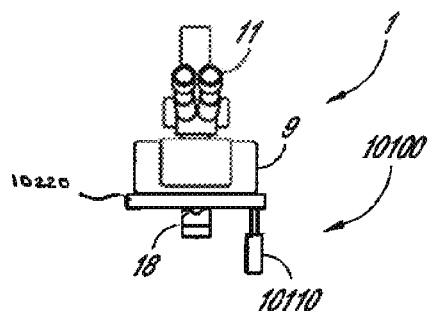
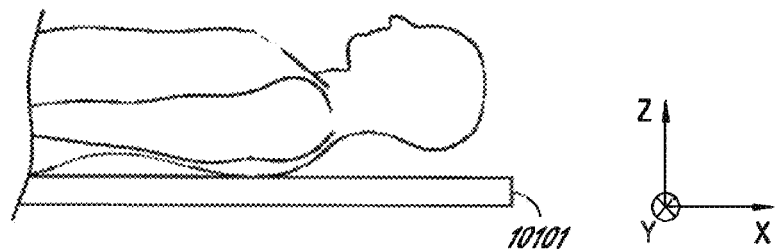
FIG. 6A
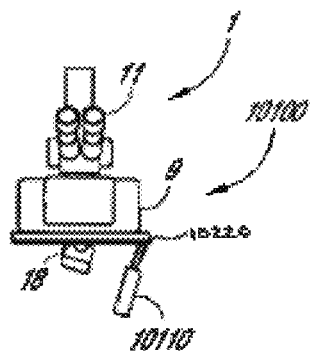
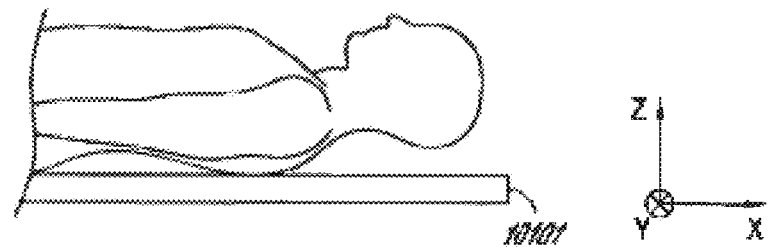
FIG. 6B

SURGICAL VISUALIZATION SYSTEMS AND DISPLAYS

CROSS-REFERENCE TO RELATED APPLICATIONS

This application claims the benefit of priority to U.S. Prov. App. No. 61/880,808, entitled "SURGICAL VISUALIZATION SYSTEMS", filed Sep. 20, 2013; to U.S. Prov. App. No. 61/920,451, entitled "SURGICAL VISUALIZATION SYSTEMS", filed Dec. 23, 2013; to U.S. Prov. App. No. 61/921,051, entitled "SURGICAL VISUALIZATION SYSTEMS", filed Dec. 26, 2013; to U.S. Prov. App. No. 61/921,389, entitled "SURGICAL VISUALIZATION SYSTEMS", filed Dec. 27, 2013; to U.S. Prov. App. No. 61/922,068, entitled "SURGICAL VISUALIZATION SYSTEMS", filed Dec. 30, 2013; and to U.S. Prov. App. No. 61/923,188, entitled "SURGICAL VISUALIZATION SYSTEMS", filed Jan. 2, 2014.

BACKGROUND

Field

Embodiments of the present disclosure relate to visualization systems and displays for use during surgery.

Description of Related Art

Some surgical operations involve the use of large incisions. These open surgical procedures provide ready access for surgical instruments and the hand or hands of the surgeon, allowing the user to visually observe and work in the surgical site, either directly or through an operating microscope or with the aide of loupes. Open surgery is associated with significant drawbacks, however, as the relatively large incisions result in pain, scarring, and the risk of infection as well as extended recovery time. To reduce these deleterious effects, techniques have been developed to provide for minimally invasive surgery. Minimally invasive surgical techniques, such as endoscopy, laparoscopy, arthroscopy, pharyngo-laryngoscopy, as well as small incision procedures utilizing an operating microscope for visualization, utilize a significantly smaller incision than typical open surgical procedures. Specialized tools may then be used to access the surgical site through the small incision. However, because of the small access opening, the surgeon's view and workspace of the surgical site is limited. In some cases, visualization devices such as endoscopes, laparoscopes, and the like can be inserted percutaneously through the incision to allow the user to view the surgical site.

The visual information available to a user without the aid of visualization systems and/or through laparoscopic or endoscopic systems contain trade-offs in approach. Accordingly, there is a need for improved visualization systems, for use in open and/or minimally invasive surgery.

SUMMARY

The systems, methods and devices of the disclosure each have innovative aspects, no single one of which is solely responsible for the desirable attributes disclosed herein.

In a first aspect, a medical apparatus is provided that includes a display housing and an opening in the display housing. The medical apparatus also includes an electronic display disposed within the display housing, the electronic display comprising a plurality of pixels configured to produce a two-dimensional image. The medical apparatus also includes a display optical system disposed within the display housing, the display optical system comprising a plurality of lens elements disposed along an optical path. The display optical system is configured to receive the two-dimensional image from the electronic display, produce a beam with a cross-section that remains substantially constant along the optical path, and produce a collimated beam exiting the opening in the display housing.

In some embodiments of the first aspect, the display optical system further comprises an optical redirection element configured to fold the optical path. In a further embodiment of the first aspect the optical redirection element comprises a mirror or a prism. In another embodiment of the first aspect, the display optical system is configured to direct light received from the electronic display to the opening in the display housing while reducing stray light.

In some embodiments of the first aspect, the display optical system further comprises a baffle configured to reduce stray light. In a further embodiment, the display optical system comprises less than or equal to four baffles. In a further embodiment, the display optical system comprises less than or equal to four mirrors. In a further embodiment, a first baffle is positioned between the electronic display and a first baffle along the optical path, the first mirror positioned prior to the plurality of lens elements along the optical path from the display to the opening. In another further embodiment, at least three baffles are positioned prior to the plurality of lens elements along the optical path from the display to the opening. In another further embodiment, at least two mirrors are positioned prior to the plurality of lens elements along the optical path from the display to the opening.

In some embodiments of the first aspect, the display optical system has an exit pupil and the electronic display is not parallel to the exit pupil. In some embodiments of the first aspect, the opening in the display housing comprises a mounting interface configured to mate with a binocular assembly for a surgical microscope. In a further embodiment, an exit pupil of the display optical system is of a same size or smaller than an entrance pupil of oculars in the binocular assembly.

In some embodiments of the first aspect, the medical apparatus further comprises a second electronic display and a second display optical system configured to provide a stereo view. In some embodiments of the first aspect, the medical apparatus further comprises processing electronics configured to communicate with the electronic display to provide images for the electronic display. In a further embodiment, the processing electronics are configured to receive images from one or more cameras on a surgical device. In a further embodiment, the processing electronics are configured to receive images from one or more cameras that provide a surgical microscope view.

In some embodiments of the first aspect, the optical path is less than or equal to 16.2 inches and a light-emitting portion of the electronic display has a diagonal measurement that is greater than or equal to 5 inches. In some embodiments of the first aspect, the optical path is less than or equal to 18.7 inches and a light-emitting portion of the electronic display has a diagonal measurement that is greater than or equal to 8 inches. In some embodiments of the first aspect, the display optical system further comprises a converging mirror. In some embodiments of the first aspect, the medical apparatus further comprises a viewing assembly comprising an objective lens, beam positioning optics, and an ocular, the viewing assembly configured to receive the collimated beam exiting the opening in the display housing. In some embodiments of the first aspect, the electronic display has a diagonal light-emitting portion between 4 inches and 9 inches. In some embodiments of the first aspect, an optical path length from the electronic display to a last element of the display optical system is at least 9 inches. In a further embodiment, the optical path length from the electronic display to the last element of the display optical system is less than 20 inches.

In a second aspect, a medical apparatus is provided that includes a viewing assembly comprising a housing and an ocular, the ocular configured to provide a view an electronic display disposed in the housing. The medical assembly includes an optical assembly disposed on the viewing assembly, the optical assembly configured to provide a surgical microscope view of a surgical site. The optical assembly includes an auxiliary video camera and a gimbal configured to couple the auxiliary video camera to the viewing assembly and configured to change an orientation of the auxiliary video camera relative to the viewing assembly. The medical apparatus includes an image processing system in communication with the optical assembly and the electronic display, the image processing system comprising at least one physical processor. The image processing system is configured to receive video images acquired by the auxiliary video camera, provide output video images based on the received video images, and present the output video images on the electronic display so that the output video images are viewable through the ocular. The gimbal is configured to adjust a pitch of the auxiliary video camera between a first position and a second position, wherein the auxiliary video camera has a first viewing angle perpendicular to a floor in the first position and a second viewing angle that is within about 10 degrees of parallel to the floor in the second position.

In some embodiments of the second aspect, the gimbal comprises two pivots. In a further embodiment, a first pivot is configured to adjust a pitch of the auxiliary video camera and a second pivot is configured to rotate the auxiliary video camera around an axis perpendicular to the floor.

In some embodiments of the second aspect, the gimbal is configured to adjust a pitch of the auxiliary video camera between the first position and a third position, wherein the auxiliary video camera has a third viewing angle in the third position that is less than or equal to 180 degrees from the first viewing angle. In some embodiments of the second aspect, the gimbal is electronically controlled. In some embodiments of the second aspect, the optical assembly is configured to provide an oblique view of a portion of a patient. In a further embodiment, an orientation of the ocular of the viewing assembly is configured to remain stationary when an orientation of the auxiliary video camera changes to provide the oblique view of the portion of the patient.

In some embodiments of the second aspect, the gimbal is configured to smoothly adjust the viewing angle of the auxiliary video camera between the first position and the second position. In some embodiments of the second aspect, the auxiliary video camera comprises a stereo video camera and the ocular comprises a pair of oculars. In some embodiments of the second aspect, the medical apparatus further comprises a camera arm attached to the viewing assembly.

In a third aspect, a medical apparatus is provided that includes a display housing. The medical apparatus includes a plurality of electronic displays disposed within the display housing, each of the plurality of electronic displays comprising a plurality of pixels configured to produce a two-dimensional image. The plurality of electronic displays are configured to present superimposed images in a field of view of a person's eye.

In some embodiments of the third aspect, the medical apparatus further comprises a binocular viewing assembly coupled to the display housing. In some embodiments of the third aspect, at least one of the plurality of electronic displays comprises a transmissive display panel. In some embodiments of the third aspect, the superimposed images comprise a video of a first portion of a surgery site that is superimposed on a video of a second portion of the surgery site, the first portion contained within the second portion. In a further embodiment, the video of the first portion is magnified relative to the video of the second portion.

In some embodiments, a medical apparatus can include a camera having a field of view that can be designed to include a surgical site, wherein the camera is designed to provide a surgical microscope view of the surgical site. In some embodiments, the medical apparatus can include a binocular viewing assembly having a housing and a plurality of oculars, the plurality of oculars designed to provide views of at least one display disposed in the housing. In some embodiments, the medical apparatus can include an image processing system designed to receive images acquired by the camera and present the output video images on the at least one display. In some embodiments, the medical apparatus can include a movement control system designed to move the camera relative to the binocular viewing assembly, the movement control system having a control member operatively coupled to the movement control system to translate the camera relative to the binocular viewing assembly along at least a first axis and a second axis and to rotate the camera relative to the binocular viewing assembly.

In a fourth aspect a medical apparatus is provided wherein a movement control system can include a translation system having a moveable platform to which the camera is attached, the moveable platform being positioned between the binocular viewing assembly and the camera and being moveable relative to the binocular viewing assembly along at least a first axis and a second axis. In some embodiments, the translation system can include an electromechanical device operatively coupled to the moveable platform.

In some embodiments of the fourth aspect, the movement control system can include a pitch-yaw adjustment system having an electromechanical device to which the camera can be attached, the pitch-yaw adjustment system designed to rotate the camera relative to the binocular viewing assembly around an axis parallel to the first axis and rotate the camera around an axis parallel to the second axis. In some embodiments, the control member is operatively coupled to the movement control system via sensors designed to detect movement of the control member, the sensors in communication with components of the movement control system In some embodiments, the control member can be operatively coupled to the movement control system via a gimbal having one or more sensors designed to detect movement of the control member, the sensors in communication with one or more components of the movement control system.

In some embodiments of the fourth aspect, the movement control system can be attached to the binocular viewing assembly. In some embodiments, the movement control system can be attached to an articulated arm. In some embodiments, the camera can be attached to the movement control system via an arm. In some embodiments, the medical apparatus can include a control system for controlling one or more electromechanical devices operatively coupled to the movement control system. In some embodiments, the control system can includes one or more pre-set positions for the movement control system In a fifth aspect, a medical apparatus is provided that includes a display, a plurality of cameras and a processor, at least one of said cameras providing a surgical microscope view, said plurality of cameras comprising a first camera configured to image fluorescence in a surgical field and a second camera configured to produce a non-fluorescence image of said surgical field, a processor configured to receive video from said plurality of cameras and to display on said display a first fluorescence video from the first of said cameras and display a second non-fluorescence video from said second of said cameras.

In some embodiments of the fifth aspect, said first and second cameras have different spectral responses. In certain embodiments of the fifth aspect, one of the said first and second cameras is sensitive to infrared and the other is not.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIGS. 3A and 3B illustrate an example surgical viewing system that includes an isocenter positioning system attached to the binocular viewing platform.

FIGS. 4A and 4B illustrate an embodiment of a surgical visualization system having an optical imaging system mounted under the binocular viewing platform.

FIG. 6A is a front view of an embodiment of a surgical visualization system, a movement control system, and an imager.

FIG. 6B is a front view of the embodiment of FIG. 6A with the movement control system and imager shifted.

DETAILED DESCRIPTION

The following description is directed to certain embodiments for the purposes of describing the innovative aspects of this disclosure. However, a person having ordinary skill in the art will readily recognize that the teachings herein can be applied in a multitude of different ways. The described embodiments may be implemented in any device or system that can be configured to provide visualization of a surgical site. Thus, the teachings are not intended to be limited to the embodiments depicted solely in the figures and described herein, but instead have wide applicability as will be readily apparent to one having ordinary skill in the art.

Surgical Visualization System

To provide improved visualization of a surgical site, a surgical device can be provided with multiple integrated cameras. Each of the cameras may capture a distinct view of the surgical site. In some embodiments, imagery from the plurality of cameras may be displayed to facilitate operation in a surgical site. Tiled, individual, and/or stitched imagery from the multiple cameras can provide the user with a view of the surgical site. The user can select the imagery to be displayed and the manner in which it is displayed for enhanced utility during surgery. As used herein, the term imagery and images includes video and/or images captured from one or more video cameras. Images from video are often referred to as video images or simply images. The term images may also refer to still images or snap shots. Video feed or video stream may also be used to describe the video images such as video images from a camera.

The video cameras may comprise, for example, CCD or CMOS sensor arrays or other types of detector arrays. A frame grabber may be configured to capture data from the cameras. For example, the frame grabber may be a Matrox Solios eA/XA, 4 input analog frame grabber board. Image processing of the captured video may be undertaken. Such image processing can be performed by, for example, the Matrox Supersight E2 with Matrox Supersight SHB-5520 with two Intel Six Core Xeon E5645 2.4 GHz processors with DDR3-1333SDRAM. This system can be designed to support eight or more camera inputs using two Matrox Solios eA/XA, 4 input, analog frame grabber boards. More or less cameras may be employed. In some implementations, a field programmable gate array ("FPGA") can be used to capture and/or process video received from the cameras. For example, the image processing can be performed by Xilinx series 7 FPGA boards. Other hardware devices can be used as well, including ASIC, DSP, computer processors, a graphics board, and the like. The hardware devices can be standalone devices or they can be expansion cards integrated into a computing system through a local computer bus, e.g., a PCI card or PCIe card.

Figure 1:
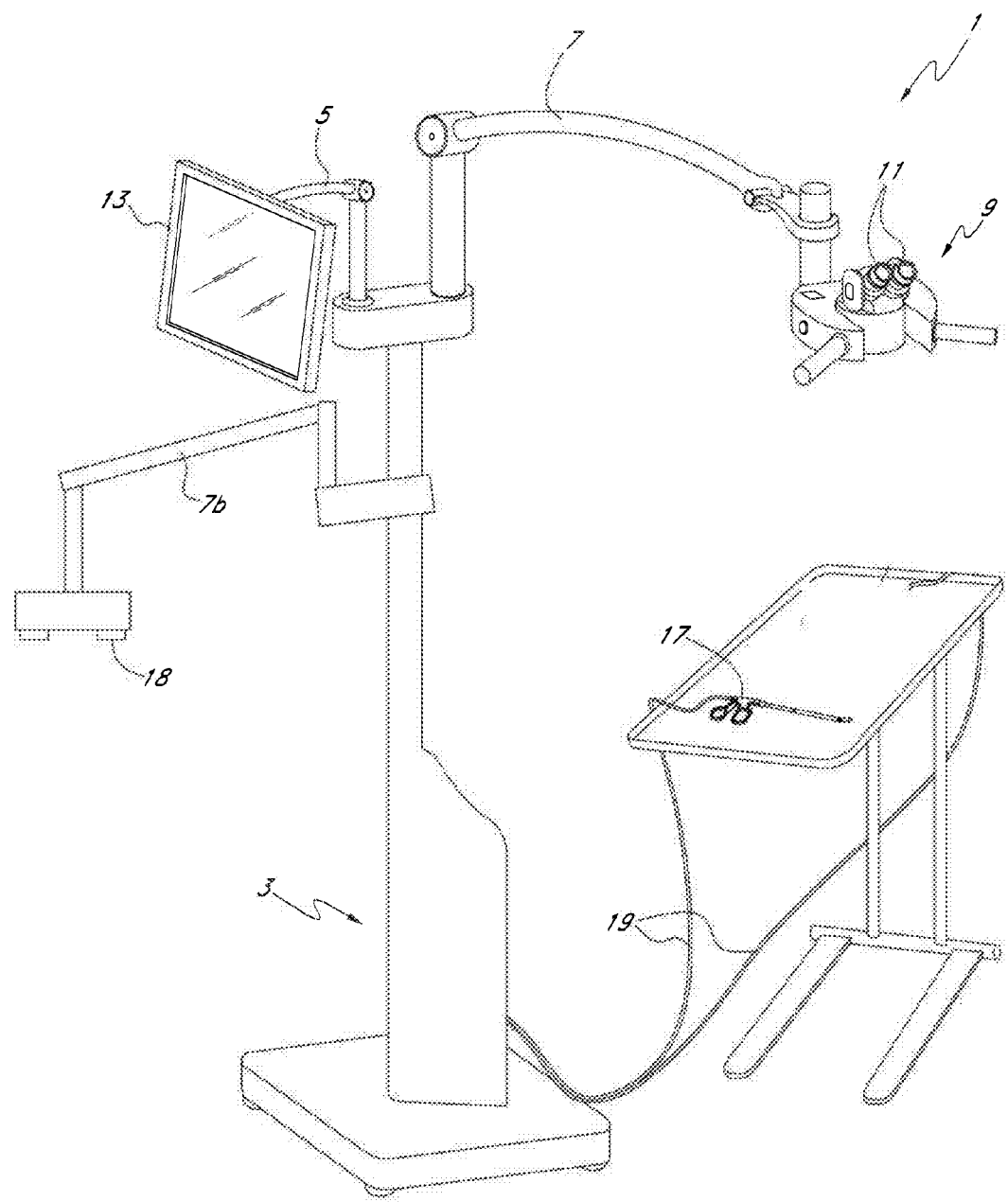
FIG. 1 illustrates an embodiment of the surgical visualization system having an imaging system that can be configured to provide imagery similar to a direct-view surgery microscope.

FIG. 1 shows an example embodiment of a surgical visualization system 1. As illustrated, the system 1 includes a console and electronics 3 from which three arms 5, 7 and 7b extend. The first arm 5 has mounted to its distal end a viewing platform 9. The viewing platform may include two oculars 11 and be configured similarly to a standard surgical microscope viewing platform. In some embodiments, however, unlike a conventional surgical microscope or a head mounted display the viewing platform 9 is not a direct view device where the surgeon or other user sees directly through the platform, e.g., an aperture in the platform. In some embodiments, regardless whether the user can view directly through the viewing platform, the surgical visualization system 1 can be configured to display video in a manner that the video displayed is decoupled from movement of the surgical microscope cameras such that a user can adjust the position and/or orientation of the surgical microscope cameras without moving the oculars 11 or the user adjusting position. As discussed in more detail below, the viewing platform 9 may include displays that receive signals from cameras that the surgeon or user employs to view the surgical site.

In some embodiments, cameras can be mounted to the viewing platform 9 and the cameras can be configured to provide imagery of the surgical site. Accordingly, the cameras can be used to provide imagery similar to a conventional surgical microscope. For example, the cameras on the viewing platform 9 can be configured to provide a working distance, or a distance from the viewing platform 9 to the patient, that can vary using zooming. The virtual working distance can vary, where the working distance can be at least about 150 mm and/or less than or equal to about 450 mm, at least about 200 mm and/or less than or equal to about 400 mm, or at least about 250 mm and/or less than or equal to about 350 mm. The working distance can be selected and/or changed by the surgeon. In some embodiments, changing the working distance does not affect the position and/or orientation of the oculars 11 with respect to the user or surgeon. In some embodiments, the cameras mounted on the viewing platform 9 can be used to provide gesture recognition to allow a surgeon to virtually interact with imagery provided by the display using the surgeon's hands, a surgical tool, or both, as described in greater detail herein.

The second arm 5 has mounted to its distal end an input and display device 13. In some embodiments, the input and display device 13 comprises a touchscreen display having various menu and control options available to a user. In some embodiments, the touchscreen can be configured to receive multi-touch input from ten fingers simultaneously, allowing for a user to interact with virtual objects on the display. For example, an operator may use the input device 13 to adjust various aspects of the displayed image. In various embodiments, the surgeon display incorporating a video camera providing a surgical microscope view may be mounted on a free standing arm, from the ceiling, on a post, or the like. The flat panel display touch screen 13 may be positioned on a tilt/rotate device on top of the electronics console.

A surgical tool 17 can be connected to the console 3 by electrical cable 19. The surgical tool 17 includes, for example, a cutting tool, a cleaning tool, a device used to cut patients, or other such devices. In other embodiments, the surgical tool 17 may be in wireless communication with the console 3, for example via WiFi (e.g., IEEE 802.11a/b/g/n), Bluetooth, NFC, WiGig (e.g., IEEE 802.11 ad), etc. The surgical tool 17 may include one or more cameras configured to provide imagery, e.g., image and/or video data. In various embodiments, video data can be transmitted to a video switcher, camera control unit (CCU), video processor, or image processing module positioned, for example, within the console 3. The video switching module may then output a display video to the viewing platform 9. The operator may then view the displayed video through the oculars 11 of the viewing platform 9. In some embodiments, the binoculars permit 3D viewing of the displayed video. As discussed in more detail below, the displayed video viewed through the viewing platform 9 may comprise a composite video formed (e.g., stitched or tiled) from two or more of the cameras on the surgical tool 17.

In use, an operator may use the surgical tool 17 to perform open and/or minimally invasive surgery. The operator may view the surgical site by virtue of the displayed video in the viewing platform 9. Accordingly, the viewing platform (surgeon display system) 9 may be used in a manner similar to a standard surgical microscope although, as discussed above, the viewing platform 9 need not be a direct view device wherein the user sees directly through the platform 9 to the surgical site via an optical path from the ocular through an aperture at the bottom of the viewing platform 9. Rather in various embodiments, the viewing platform 9 includes a plurality of displays, such as liquid crystal or light emitting diode displays (e.g., LCD, AMLCD, LED, OLED, etc.) that form an image visible to the user by peering into the ocular. Accordingly, one difference, however, is that the viewing platform 9 itself need not necessarily include a microscope objective or a detector or other image-capturing mechanisms. Rather, the image data can be acquired via the cameras of the surgical tool 17. The image data can then be processed by a camera control unit, video processor, video switcher or image processor within the console 3 and displayed imagery may then be viewable by the operator at the viewing platform 9 via the display devices, e.g., liquid crystal or LED displays, contained therein. In some embodiments, the viewing platform 9 can provide a view similar to a standard surgical microscope using cameras and displays and can be used in addition to or in conjunction with a standard surgical microscope optical pathway in the viewing platform. In certain embodiments, the viewing platform 9 can provide a surgical microscope view wherein changes in the viewing angle, viewing distance, work distance, zoom setting, focal setting, or the like is decoupled from movement of the viewing platform 9. In certain embodiments, changes in the position, pitch, yaw, and/or roll of the imaging system 18 are decoupled from the viewing platform 9 such that the imaging system 18 can move and/or re-orient while the surgeon can remain stationary while viewing video through the oculars 11.

The third arm 7b can include an imaging system 18 that can be configured to provide video similar to a direct-view surgery microscope. The imaging system 18 can be configured, then, to provide a surgical imaging system configured to provide an electronic microscope-like view that can comprise video of the work site or operational site from a position above the site (e.g., about 15-45 cm above the surgical site) or from another desired angle. By decoupling the imagers 18 from the display, the surgeon can manipulate the surgical imaging system to provide a desired or selected viewpoint without having to adjust the viewing oculars. This can advantageously provide an increased level of comfort, capability, and consistency to the surgeon compared to traditional direct-view operating microscope systems. In some embodiments, as described herein, the imagers 18 can be located on the viewing platform 9, on a dedicated arm 7b, on a display arm 5, on a separate post, a separate stand, supported from an overhead structure, supported from the ceiling or wall, or detached from other systems. The imagers 18 can comprise a camera configured to be adjustable to provide varying levels of magnification, viewing angles, monocular or stereo imagery, convergence angles, working distance, or any combination of these.

The viewing platform 9 can be equipped with wide field-of-view oculars 11 that are adjustable for refractive error and presbyopia. In some embodiments, the oculars 11, or eyepieces, may additionally include polarizers in order to provide for stereoscopic vision. The viewing platform 9 can be supported by the arm 7 or 7b, such that it may be positioned for the user to comfortably view the display 13 through the oculars 11 while in position to perform surgery. For example, the user can pivot and move the arm 7 or 7b to re-orient and/or re-position the viewing platform 9.

In some embodiments, the image processing system and the display system are configured to display imagery placed roughly at infinity to reduce or eliminate accommodation and/or convergence when viewing the display. A display optical system can include one or more lenses and one or more redirection elements (e.g., mirrors, prisms) and can be configured to provide light from the display that can be imaged by a binocular viewing assembly comprising a pair of oculars, objectives, and/or turning prisms or mirrors. The display devices such as liquid crystal displays can be imaged with the objective and the pair of oculars and display optical system within the viewing platform 9. The binocular assembly and display optical system can be configured to produce an image of the displays at infinity. Such arrangements may potentially reduce the amount of accommodation by the surgeon. The oculars can also have adjustments (e.g., of focus or power) to address myopia or hyperopia of the surgeon. Accordingly, the surgeon or other users may view the displays through the oculars without wearing glasses even if ordinarily prescription glasses were worn for other activities.

Figure 2:
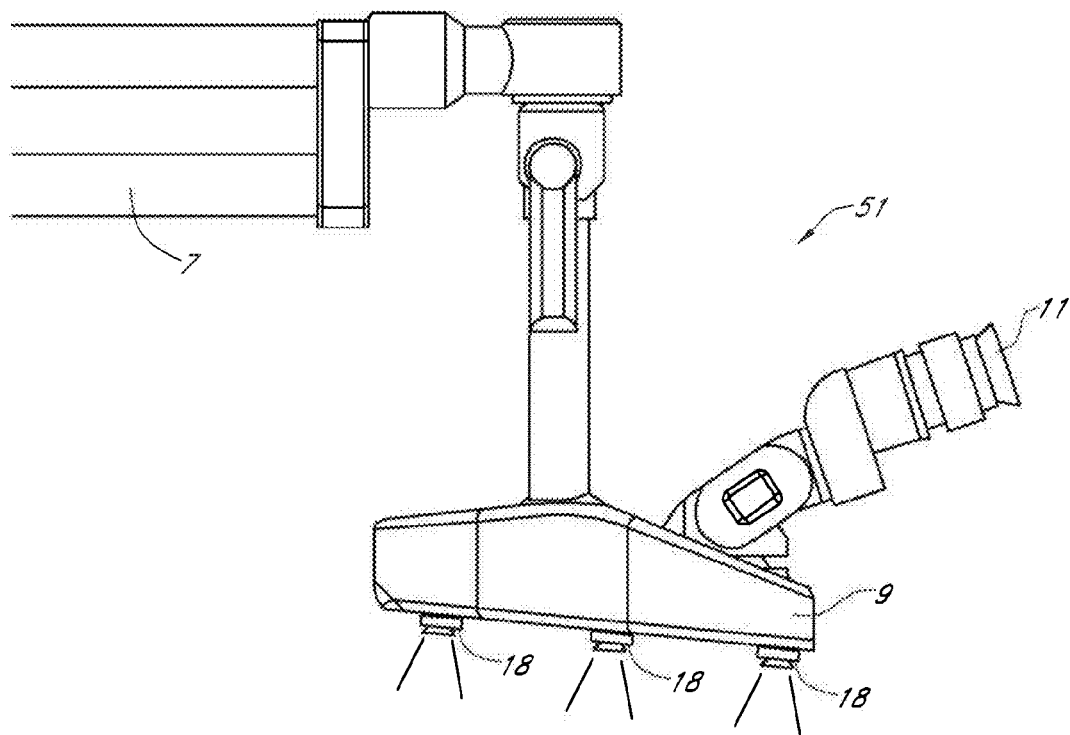
FIG. 2 illustrates an example surgical viewing system attached to an articulating arm, the system including one or more cameras mounted on a binocular viewing platform.

In some embodiments, the viewing platform 9 can include one or more imagers configured to provide electronic microscope-like imaging capabilities. FIG. 2 illustrates an example surgical imaging system 51 attached to an arm 7, the system 51 including one or more cameras 18 mounted on a viewing platform 9. The cameras 18 can be configured to provide imagery of a worksite. The image data can be presented on a display that the user can view using oculars 11 mounted on the viewing platform 9. This design can be used to mimic other direct-view microscopes, but it can also be configured to provide additional capabilities. For example, the surgical imaging system 51 can be configured to have a variable working distance without adjusting the viewing platform 9 or the articulating arm 7. The surgical imaging system 51 can be configured to provide image processing capabilities such as electronic zooming and/or magnification, image rotation, image enhancement, stereoscopic imagery, and the like. Furthermore, the imagery from the cameras 18 can be combined with imagery from cameras on the surgical device 17. In some embodiments, the surgical imaging system 51 can provide fluorescence images.

Although the discussion considers images from surgical tools, numerous embodiments may involve at least one auxiliary video camera 18 and one or more other cameras that are not disposed on surgical tools but are disposed on other medical devices. These medical devices may include devices introduced into the body such as endoscopes, laparoscopes, arthroscopes, etc.

Accordingly, one or more displays such as the at least one display 13 included in the viewing platform 9 may be used to provide a surgical microscope view using one or more cameras such as the auxiliary video camera(s) 18 as well as to display views from one or more cameras located on such medical devices other than surgical tools. In some embodiments, cameras from a variety of sources, e.g., surgical tools and other medical devices, in any combination, may be viewed on the display(s) on the surgical platform together with the surgical microscope view from the auxiliary video cameras 18. As described herein, the displays may provide 3D thus any of the images and graphics may be provided in 3D.

In various embodiments, a virtual touchscreen may be provided by the auxiliary video cameras 18 or other virtual touchscreen cameras mounted to the viewing platform 9. Accordingly, in some embodiments a user may provide a gesture in the field of view of the auxiliary video cameras and/or virtual touchscreen cameras and the processing module can be configured to recognize the gesture as an input. Although the virtual display has been described in the context of the auxiliary video cameras 18, other cameras, e.g., virtual reality input cameras, possibly in addition to the auxiliary video cameras 18 may be used. These cameras may be disposed on the viewing platform 9 or elsewhere, such as the third arm 7b. As described herein the displays may provide 3D thus the virtual reality interface may appear in 3D. This may increase the immersive quality of the viewing experience, enhancing the detail and/or realistic presentation of video information on the display.

Figure 3A:
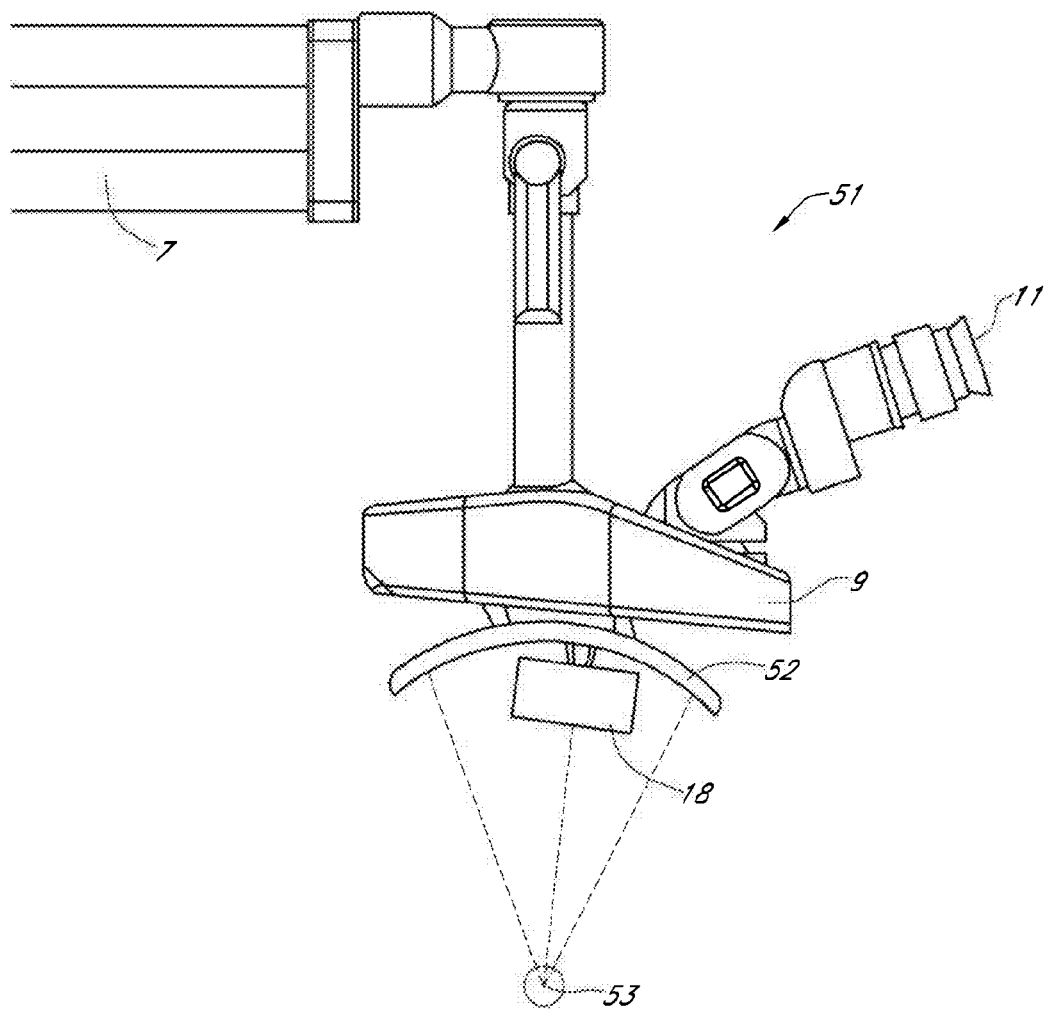

In some embodiments, as illustrated in FIG. 3A, the surgical imaging system 51 includes an isocenter positioning system 52 attached to the viewing platform 9. The isocenter positioning system 52 can include a single track or guide configured to move and orient the cameras 18 such that they are substantially pointed at a single point 53, the isocenter. In some embodiments, a second track or guide can be attached to the first guide in an orthogonal manner to provide movement along two dimensions while substantially maintaining the pointing angle towards the isocenter 53. Other configurations can be used to provide isocenter pointing capabilities, such as articulating arms, electro-mechanical elements, curved friction plates, etc. In some embodiments, as illustrated in FIG. 3B, the imaging system is configured to move in an isocenter manner. This can be used to enhance dexterity of the user of the system because hand-eye coordination is increased or maximized. Such enhanced dexterity can be vital for prolonged and/or difficult surgery. In the displayed embodiment, the horizons of the acquisition systems are configured to be horizontal to match the horizon of the display system and the user. As shown in FIG. 3B, in various embodiments, a stereo imaging system may be maintained in a horizontal configuration as it is moved across a range of locations to avoid confusion for the user viewing the video from the stereo camera. By maintaining a common relative horizon between the display and the acquisition system, the user can relatively easily translate hand motion to manipulation of objects in the display, which may not be the case where translation of the acquisition is accompanied by a relative rotation between the display and the acquisition system.

In the embodiments illustrated in FIGS. 3A and 3B, the isocenter assemblies can be a part of the display system or a separate, independent system. For example, the viewing platform 9 can be mounted on a separate arm from the cameras 18. Thus, the display and the image acquisition of the surgical imaging system can be decoupled, similar to the embodiment illustrated in FIG. 1. By decoupling the isocenter cameras 18 from the display ergonomic benefits are provided such as, for example, the surgeon does not need to be looking through binoculars for an extended period of time or at an uncomfortable position or angle. In various embodiments, a common relative horizon for both the display and the acquisition system may also be employed.

In some embodiments, the distance between the surgical site of interest and the imagers, e.g., the working distance, can be at least about 20 cm and/or less than or equal to about 450 cm, at least about 10 cm and/or less than or equal to about 50 cm, or at least about 5 cm and/or less than or equal to about 1 m, although values outside this range are possible.

The user can interact with the surgical imaging system 51 to select a working distance, which can be fixed throughout the procedure or which can be adjusted at any point in time. Changing the working distance can be accomplished using elements on a user interface, such as a graphical user interface, or using physical elements such as rotatable rings, knobs, pedals, levers, buttons, etc. In some embodiments, the working distance is selected by the system based at least in part on the cables and/or tubing being used in the surgical visualization system. For example, the cables and/or tubing can include an RFID chip or an EEPROM or other memory storage that is configured to communicate information to the surgical imaging system 51 about the kind of procedure to be performed. For an ENT/Head/Neck procedure, the typical working distance can be set to about 40 cm. In some embodiments, the user's past preferences are remembered and used, at least in part, to select a working distance.

In some embodiments, gross focus adjustment can be accomplished manually by positioning the cameras 18 and arm 7. The fine focus adjustment can be done using other physical elements, such as a fine focusing ring, or it can be accomplished electronically.

In some embodiments, the magnification of the surgical imaging system 51 can be selected by the user using physical or virtual user interface elements. The magnification can change and can range between about 1× and about 6×, between about 1× and about 4×, or between about 1× and about 2.5×. Embodiments may be able to change between any of these such as between 2.5× and 6× or between 2.5× and 6×. Values outside these ranges are also possible. For example, the system 51 can be configured to provide magnification and demagnification and image inversion, with a range from about −2× to about 10×, from about −2× to about 8×, from about −2× to about 4×, from about −0.5× to about 4×, or from about −0.5× to about 10×. The surgical imaging system 51 can be configured to decouple zoom features and focus adjustments, to overcome problems with traditional operating room microscopes. In some embodiments, the surgical visualization system 51 can be used to provide surgical microscope views. In some embodiments, the surgical imaging system 51 can decouple instrument myopia by providing an electronic display instead of a direct view of a scene. The electronic displays can be configured to be focused at varying levels of magnification allowing the user to view the displays without adjusting the oculars between magnification adjustments. Moreover, in various embodiments, the oculars can be configured to provide continuous views at infinity. In some embodiments, however, the principal user of the surgical imaging system may select an accommodation level for the oculars, rather than using a relaxed view provided by the electronic displays. The electronic displays, in various embodiments, however, can remain in focus and the ocular adjustments do not affect the focus of the various video acquisition systems. Thus, adjustments by the principal user do not affect the views of the other users of the system viewing, for example, other displays showing the video, as the cameras/acquisition systems can remain focused. In some embodiments, the surgical imaging system 51 can be focused at a relatively close working distance (e.g., a distance with a relatively narrow depth of field) such that the image remains focused when moving to larger working distances (e.g., distances with broader depth of field). Thus, the surgical imaging system 51 can be focused over an entire working range, reducing or eliminating the need to refocus the system after magnification or zoom adjustments are made.

FIGS. 4A and 4B illustrate an embodiment of the surgical imaging system 51 having an optical system 53 mounted under the viewing platform 9. As illustrated, the optical components are shown as free-standing to show the structure of the components, but in practice the optical components 53 will be mounted within or on a structure attached to the viewing platform. In some embodiments, the optical system 53 and/or the cameras 18 (discussed above) can be modular and can be selected and swapped for use with the surgical imaging system 51. Paragraph [0489] from each of U.S. Prov. App. No. 61/880,808, U.S. Prov. App. No. 61/920,451, U.S. Prov. App. No. 61/921,051, U.S. Prov. App. No. 61/921,389, U.S. Prov. App. No. 61/922,068, and U.S. Prov. App. No. 61/923,188 is incorporated by reference herein.

The optical system 53 is configured to provide stereo image data to the imaging system 51. The optical system 53 includes a turning prism 54 to fold the optical path underneath the viewing platform 9 to decrease the physical extent (e.g., length) of the imaging system under the viewing platform 9.

In some embodiments, the optical system 53 comprises a Greenough-style system wherein the optical paths for each eye have separate optical components. In some embodiments, the optical system 53 comprises a Galilean-style system wherein the optical paths for each eye pass through a common objective. The Greenough-style system may be preferable where imaging sensors are being used to capture and convey the image data as compared to the Galilean-style system. The Galilean system can introduce aberrations into the imagery by virtue of the rays for each eye's optical path passing through a periphery of the objective lens. This does not happen in the Greenough-style system as each optical path has its own optics. In addition, the Galilean system can be more expensive as the objective used can be relatively expensive based at least in part on the desired optical quality of the lens and its size.

The optical system 53 can include two right-angle prisms 54, two zoom systems 55, and two image sensors 56. This folding is different from a traditional operating room microscope because the optical path leads to image sensors rather than to a direct-view optical system.

In some embodiments, the optical system 53 can have a relatively constant F-number. This can be accomplished, for example, by varying the focal length and/or aperture of the system based on working distance and/or magnification. In one embodiment, as the focal length changes, the eye paths can move laterally apart (or together), the prisms 54 can rotate to provide an appropriate convergence angle, and the apertures can change their diameters to maintain the ratio of the focal length to the diameter a relatively constant value. This can produce a relatively constant brightness at the image sensor 56, which can result in a relatively constant brightness being displayed to the user. This can be advantageous in systems, such as the surgical visualization systems described herein, where multiple cameras are being used and changing an illumination to compensate for changes in focal length, magnification, working distance, and/or aperture can adversely affect imagery acquired with other cameras in the system. In some embodiments, the illumination can change to compensate for changes in the focal length and/or the aperture so as to provide a relatively constant brightness at the image sensors 56.

The optical assembly 53 can include a zoom system 55 configured to provide a variable focal distance and/or zoom capabilities. A Galilean-style stereoscopic system generally includes a common objective for the two eye paths. When this optical system is imaged with image sensors 56, it can create aberrations, wedge effects, etc. that can be difficult to compensate for. In some embodiments, the surgical imaging system 51 can include a Galilean-style optical system configured to re-center at least one of the stereo paths to a central location through the objective lens, which can be advantageous in some applications.

In some embodiments, the real-time visualization system utilizes a Greenough-style system. This can have separate optical components for each stereo path. The optical assembly 53 can be configured to provide variable magnification and/or afocal zoom and can be configured to operate in a magnification range from about 1× to about 6×, or from about 1× to about 4×, or from about 1× to about 2.5×.

The distal-most portion of the Greenough assembly 53 can be similar in functionality to an objective lens of a typical, direct-view operating room microscope with the working distance set approximately to that of the focal length. The working distance, and in some implementations the focal length, can be between about 20 cm and about 40 cm, for example. In some embodiments the work distance may be adjustable from 15 cm to 40 cm or to 45 cm. Other values outside these ranges are also possible. In some embodiments, the surgical imaging system 51 includes an opto-mechanical focus element configured to vary the focal length of a part of the optical assembly 53 or the whole optical assembly 53.

Figure 5A:
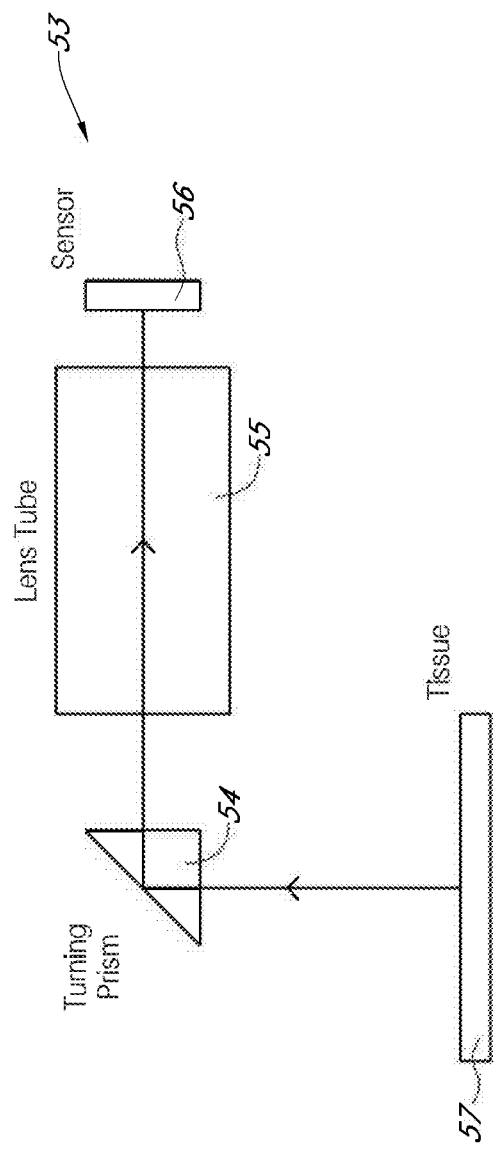
FIGS. 5A-5E illustrate embodiments of optical imaging systems for use in a stereoscopic surgical viewing system, such as those illustrated in FIGS. 4A and 4B.

FIGS. 5A-5E illustrate embodiments of optical assemblies 53 for use in a stereoscopic surgical imaging system, such as those described herein with reference to FIGS. 4A-4B. FIG. 5A illustrates a side view of an example optical assembly 53 configured to use a turning prism 54 to fold an optical path from a tissue 57 to a sensor 56 along a lens train 55 that is situated near or adjacent to a viewing platform 9. This can advantageously provide a relatively long optical path in a relatively compact distance.

Figure 5B:
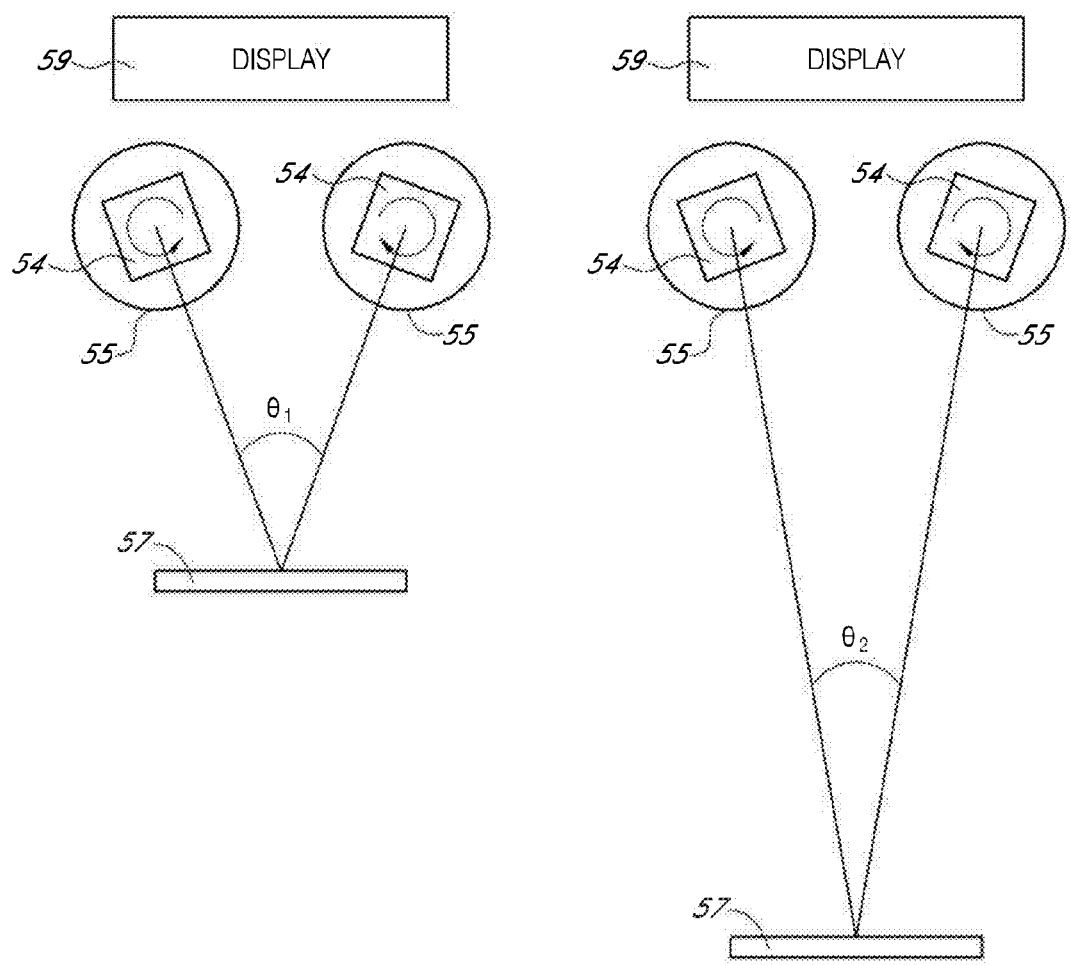

FIG. 5B illustrates a front view of an embodiment of an optical assembly configured to change a convergence angle in a stereoscopic imaging system. The prisms 54 can be the turning prism 54 illustrated in FIG. 5A. The prisms 54 can be configured to rotate to change a convergence angle, and as a result, a convergence point and/or a working distance. The working distance, which can be a distance from the prisms 54 to the target 57 (e.g., tissue), can be user-selectable or adjustable. In various embodiments, with increased working distance to the target 57, the convergence angle can decrease. Conversely, when the working distance gets smaller, the convergence angle can increase (e.g., $\theta 1 > \theta 2$). This can be advantageous where the lens path 55 is fixed and the working distance is adjustable. The stereo imagery can then be viewed on the display 59 by a user.

Figure 5C:
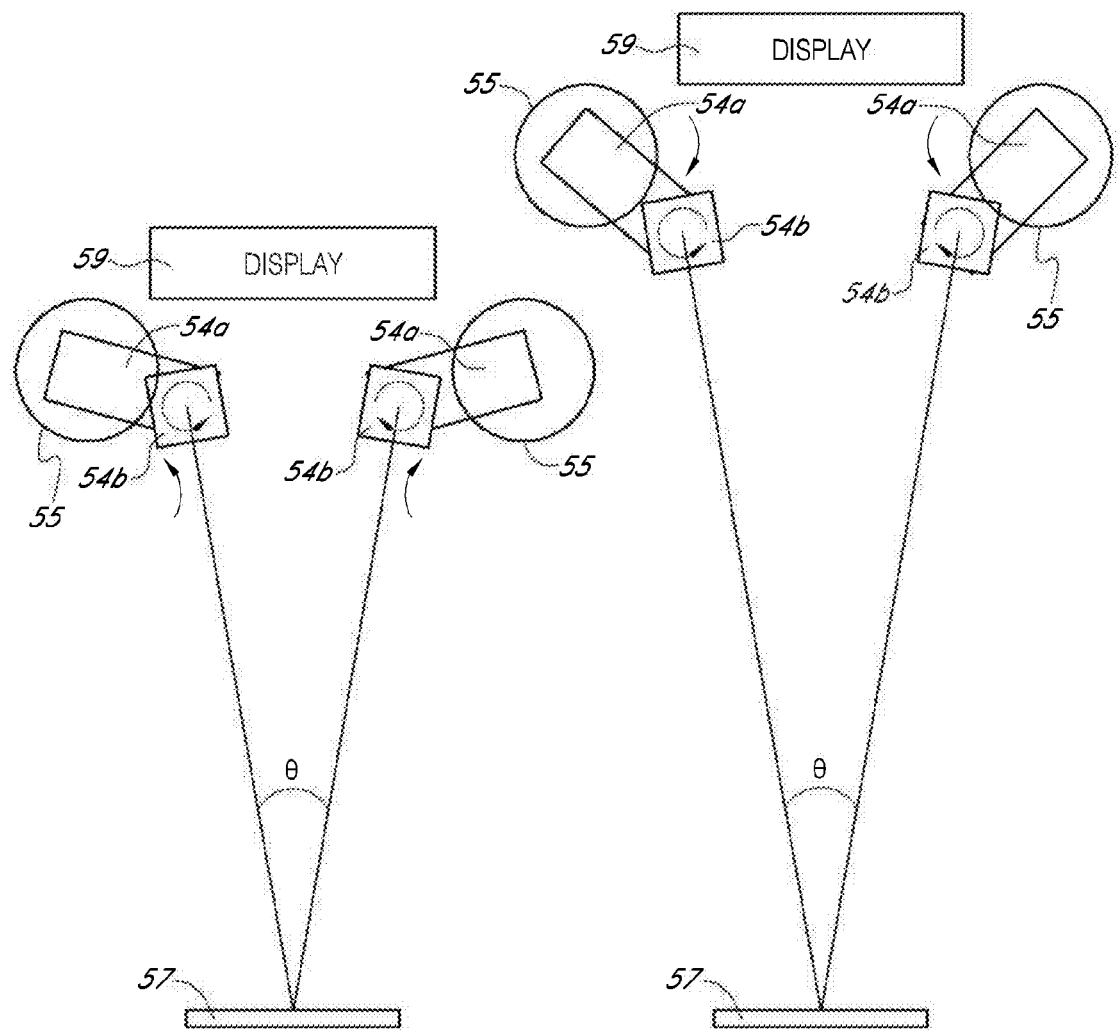

FIG. 5C illustrates a front view of an embodiment of an optical assembly 53 that is configured to maintain a substantially constant convergence angle. The optical assembly 53 can include two prisms 54a and 54b for each optical path, wherein the prisms 54a, 54b can move and/or rotate. For example, when the working distance decreases the first set of prisms 54a can rotate towards one another to decrease an effective distance between the second set of prisms 54b. The second set of prisms 54b can, in turn, rotate to compensate for the changed angle so as to converge on the common target. The second set of prisms 54b can direct the light to the first set of prisms 54a which can then direct the light down the fixed lens paths 55 (e.g., fixed in their position relative to the viewfinder). By providing a relatively fixed convergence angle, a change in working distance may not require refocusing for the user. Maintaining a constant convergence angle, especially a comfortable angle, may reduce the strain on the user such as a surgeon performing a prolonged, arduous procedure.

Figure 5D:
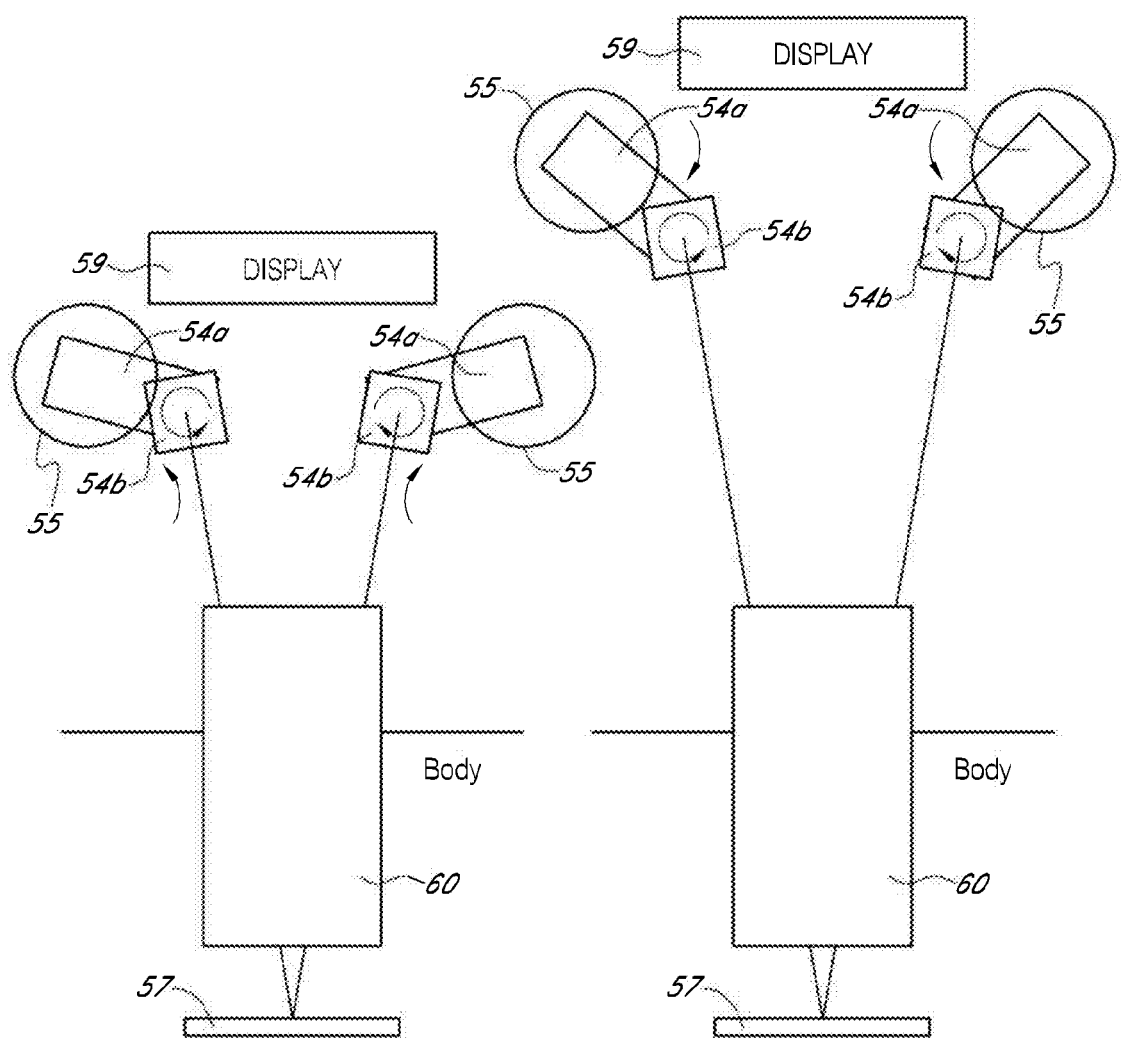

FIG. 5D illustrates a front view of an embodiment of an optical assembly 53 configured to provide a substantially narrow convergence angle to be able to view stereoscopic imagery through a narrow insertion tube 60 (e.g., a tube partially inserted into a body during a procedure). A similar assembly 53 can be used as described with reference to FIG. 5C, and the convergence angle can be maintained substantially constant or at least sufficiently narrow to view through the insertion tube 60.

Figure 5E:
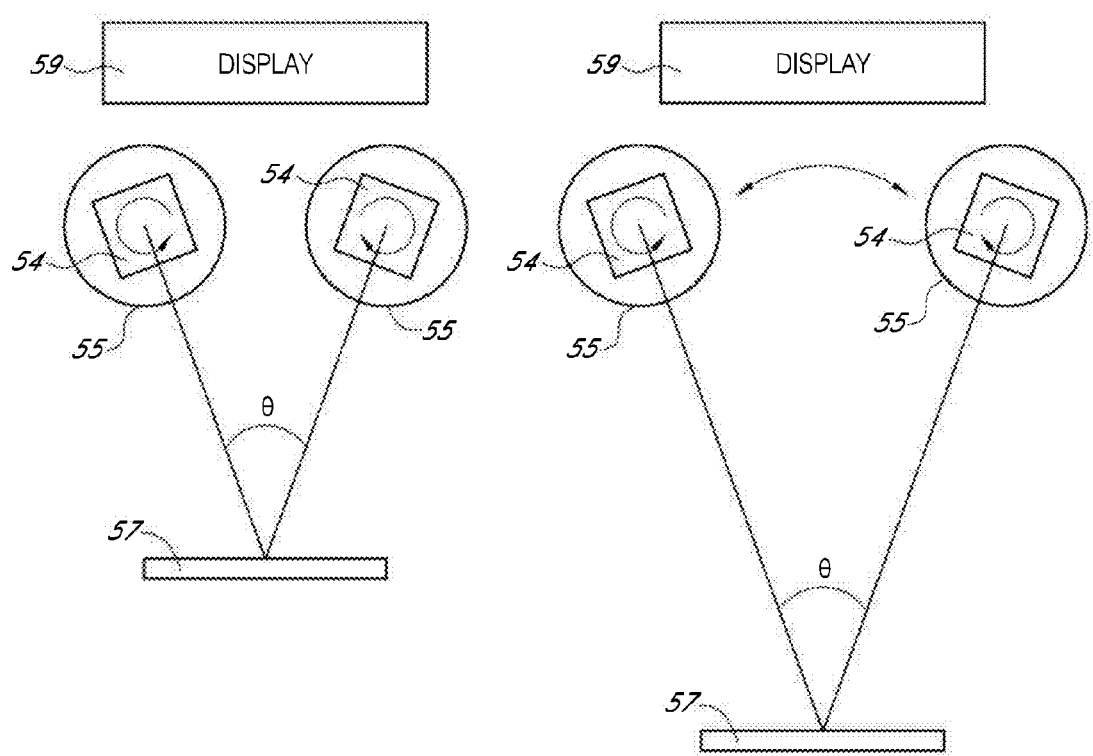

FIG. 5E illustrates a front view of an embodiment of an optical assembly 53 configured to provide a substantially constant convergence angle by moving the lens paths 55 laterally, e.g., toward or away from one another. The prisms 54 can be made to have a substantially constant orientation (e.g., no rotation for changing working distances) and compensation for changing working distance can be accomplished by translating the optical paths laterally to separate or join the optical paths. The translation of the optical paths can be accomplished using any suitable means including, for example, electro-mechanical actuators, slides, articulating arms, etc. This can simplify the optical assembly compared to the embodiments having two sets of prisms as only one set of prisms may be used when the lens paths are configured to move.

The embodiments of the optical assembly 53 which are configured to maintain a sufficiently narrow convergence angle can be advantageous as they allow stereo access to narrow surgical entries by allowing the angle to decrease and avoid clipping one of the stereo paths. For example, the left and right lens paths can move closer to one another and the prisms can adjust to the proper convergence angle for that distance. As another example, the left and right lens paths can remain fixed and there can be sets of prisms for each path configured to direct the light along the lens paths while maintaining a substantially constant convergence angle. In some embodiments, maintaining a constant convergence angle can be visually helpful to the user when zoom changes, e.g., because the changing depth cues do not confuse the user's eye and/or brain. In addition, constant convergence may induce less stress on the user.

Movement Control System

Figure 6C:
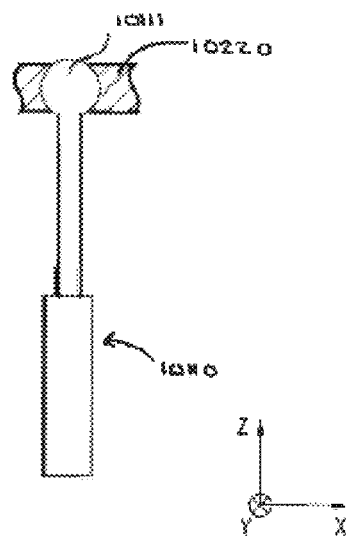
FIG. 6C is a partial section view of the embodiment of a movement control system of FIG. 6A.

FIGS. 6A-C illustrate embodiments of components of a movement control system 10100 that can be configured to allow an operator of the surgical visualization system 1, such as a medical professional or assistant, to control the movement of one or more imagers 18. Such imagers may comprise cameras that provide a surgical microscope view through the oculars 11 or eyepieces of the binocular display unit 9. In various embodiments, the movement control system can enable the imagers 18 to be moved without changing the positioning of oculars 11, and thus an operator can remain in an ergonomic position while changing the view provided by the imager 18. The imager 18 can be on the binocular display unit 9 or located elsewhere such as on a separate platform or articulated arm. Additionally, unlike conventional articulated optical systems which are generally unwieldy, complex, and have the potential for introducing optical aberrations, use of the movement control system 10100 with the surgical visualization system 1 can result in a simplified system with greater optical clarity and range of movement. It should be appreciated by one of skill in the art that, while the description of the movement control system 10100 is described herein in the context of medical procedures, the movement control system 10100 can be used for other types of visualization and imaging systems. Movement of the imagers 18 can be performed prior to and/or during the activity, such as surgical procedures, dental procedures, and the like. Movement of the imagers 18 can advantageously allow a medical professional or other operator to alter the view through oculars 11, for example, to provide different surgical microscope-like electronic visualizations which might be beneficial during the course of a medical procedure or for different surgical procedures.

In some embodiments, control of the movement of the imager 18 can be achieved using a single control member such as 10110. This provides the advantage of allowing single-handed operation of the movement control system 10100 which can, for example, allow a medical professional to move one or more imagers 18 using only one hand while using a second hand for other tasks such as performing surgical techniques. It should be appreciated by one of skill in the art that, while the description of the movement control system 10100 is described herein in the context of medical procedures, the movement control system 10100 can be used for other types of visualization and imaging systems.

Operation

As illustrated in FIGS. 6A-C, in some embodiments, the control member, such as a joystick, 10110 can be used to translate the imager 18, adjust the pitch, yaw, and/or roll of the imager 18, and/or adjust the working distance of the imager 18. In some embodiments, the oculars 11 can remain immobile when translating the imager 18, adjusting the pitch, yaw, and/or roll of the imager 18, and/or adjusting the working distance of the imager 18. The ability for a single control member 10110 to control translation, adjustments to pitch and/or yaw, and/or adjustments to the working distance can beneficially simplify operation of the device as an operator need not release the control member 10110 to control multiple aspects of its operation. For example, an operator can translate the imager 18 and subsequently adjust the pitch and/or yaw without having to release the control member 10110 thereby increasing ease-of-use of the system and enhancing efficiency when using this system.

As shown in FIG. 6C, one or more control members of the movement control system 10100, such as control member 10110, and/or one or more imager arms (see FIG. 7) can be attached to a component of the movement control system 10100 using various types of joints and/or can be remote from the movement control system 10100 such as a remote joystick or toggle. In some embodiments, the control member 10110 can include a joint for attachment to the movement control system 10100. For example, as shown in the illustrated embodiment, control member 10110 can include joint 10111. In some embodiments, one or more of the joints can include components for detecting movement of the control member and/or an imager arm. For example, one or more of the joints can include one or more sensors for detecting rotation and/or translation of the control member and/or the imager arm about the joint. The signals from these sensors can be used to control other components of the movement control system, such as one or more electromechanical components.

For purposes of this disclosure, rotation about joints, such as joint 10111, around the x-axis is hereinafter termed "pitch" or "tilt" and rotation about joints, such as joint 10111, around the y-axis is hereinafter termed "yaw" or "pan."

As shown in the illustrated embodiment, the joint 10111 can be spherical joints received in a socket formed in the member 10220 thereby forming a ball-and-socket attachment. As should be apparent to one of ordinary skill in the art, other types of mounting mechanisms may be used for attaching control member 10110 as well as an imager arm to components of the movement control system 10100. For example, joints such as gimbals can be used which limit the rotational degrees of freedom about the gimbal. Other types of joint can be used depending on the types of movement the movement control system is designed to allow. For example, if only pitch is needed without yaw, one can use a joint having a single rotational degree of freedom. In some embodiments, the control member 10110 can be positioned remotely from the movement control system 10100.

General Embodiment

With continued reference to FIGS. 6A and 6B, in some embodiments, the movement control system 10100 can be attached to an attachment structure, such as binocular display unit 9, and support one or more imagers 18. As shown in the illustrated embodiment, the movement control system 10100 can be oriented generally underneath the binocular display unit 9 and in some embodiments can be sized such that the movement control system 10100 does not extend significantly beyond the outer housing of the binocular display unit 9. This can advantageously provide a smaller form factor thereby reducing the likelihood that the movement control system 10100 will interfere with the medical professionals and assistants during a medical procedure. In other embodiments, the attachment structure can be other components of the surgical visualization system 1 such as, but not limited to, a dedicated articulating arm or a display arm. In some embodiments, the movement control system 10100 can extend significantly beyond the outer housing of the binocular display unit 9 or any other platform to which it is attached. This can be advantageous in situations where a greater degree of movement of the imagers 18 is desired or in embodiments where the control member 10110 is located above the attachment point between the movement control system 10100 and binocular display unit 9.

With continued reference to FIGS. 6A and 6B, as discussed in part above, the movement control system 10100 can be configured to allow translation of one or more attached imagers 18 along a plane relative to the binocular display unit 9. In some embodiments, the binocular display unit 9 can be immobile while the one or more imagers 18 are translated. For example, when attached to the binocular display unit 9 with the movement control mechanism 10100 parallel to an operating table 10101, the one or more imagers 18 can be translated along a plane parallel to the operating table 10101. As shown in the illustrated embodiment, the movement control system 10100 can be translated along both the x-axis and the y-axis (which projects perpendicularly through the sheet). This can advantageously allow the medical professional to position the view of oculars 11 for comfortable viewing by the surgeon thereby reducing physical strain on the surgeon during long procedures.

In some embodiments, defining an imager 18 centered on the movement control system 10100 (as shown in FIG. 6A) as having an x-axis, y-axis, and z-axis coordinate of zero, the movement control system 10100 can have a range of translation relative to the binocular display unit 9, of approximately ±500 mm along the x-axis and y-axis at full extension, approximately ±400 mm along the x-axis and y-axis at full extension, approximately a ±300 mm along the x-axis and y-axis at full extension, approximately ±200 mm along the x-axis and y-axis at full extension, or approximately ±100 mm along the x-axis and y-axis at full extension. In some embodiments, full extension along one axis can be greater than full extension along the other axis. For example, in some embodiments, full extension along the x-axis may be approximately ±175 mm whereas the y-axis extension can be three-quarters full extension of the x-axis, one-half full extension of the x-axis, one-quarter full extension of the x-axis, or any other ratio between unity and zero. In some embodiments, the range of translation relative to the binocular display unit 9 along the y-axis can be approximately ±87.5 mm. This can be advantageous in cases where allowing the y-axis to have a full range of motion may interfere with the medical professional and/or assistants.

These ratios can be reversed such that the range of translation of the x-axis can be three-quarters full extension of the y-axis, one-half full extension of the y-axis, one-quarter full extension of the y-axis, or any ratio between unity and zero. Additionally, in some embodiments, the imager 18 can translate further in the "positive" direction than the "negative" direction. For example, along the x-axis, the imager 18 may move from −100 mm to 500 mm. Ranges of motion outside these ranges are also possible. As should be apparent to one of ordinary skill in the art, the maximum translation relative to the binocular display unit 9 along the x-axis and y-axis can be chosen to provide a balance between greater maneuverability, the yaw and/or pitch angles, working distances, size constraints, and other such factors.

As described in part above and as will be discussed in greater detail below, in some embodiments, translation of the imagers 18 can be performed by translating one or more control members, such as control member 10110, in the desired direction. In some embodiments, the control member 10110 can be electrically coupled to the movement control system 10100 to provide translation via an electromechanical system utilizing stepper motors, linear motors, or the like. For example, a joint of the control member 10110 can include components for detecting translation of the control member 10110. The signals from these sensors can be used to control other components of the movement control system, such as one or more electromechanical components such as stepper motors, linear motors, or the like to translate the imager 18. The electromechanical components can be coupled to a moveable platform to which the imager 18 can be attached. In some embodiments, the control member 10110 can be physically connected to the movement control system 10100 without any electromechanical assistance.

As should be appreciated by one of ordinary skill in the art, the movement control system 10100 need not translate solely along a plane parallel to the operating table 10101 or the x-y plane as set forth in the illustrated embodiment. In some embodiments, the plane of translation can be defined by the orientation of the mount to which the movement control system 10100 is connected. In some embodiments, the movement control system 10100 can be configured for non-planar translation and/or translation along more than one plane. In some embodiments, for example, a tip and tilt stage provides angular motion. A rotary stage can also be used to provide rotary motion.

With continued reference to FIGS. 6A and 6B, as described in part above, the movement control system 10100 can be configured to allow rotation of the one or more attached imagers 18 about a joint which can be attached to components of the movement control system 10100 and/or remotely from the movement control system 10100. In some embodiments, the movement control system 10100 can be designed to allow the control member, such as control member 10110, as well as the imager 18 and/or imager armto "pitch" or "tilt" and "yaw" or "pan" relative to the binocular display unit 9. In some embodiments, the binocular display unit 9 can be immobile while the "tilt" and "yaw" or "pan" of the one or more imagers 18 are adjusted. Pitch or yaw can allow the imager 18 to have a line of sight that is centered (e.g., focused) on the surgical site after the imager 18 is translated. This can advantageously allow the medical professional or assistant to adjust the viewing angle during a medical procedure. This can be beneficial in circumstances where a medical professional is unable to adequately view an object due to another element obstructing the view. Under such circumstances, a medical professional can translate the imager 18 and adjust the viewing angle of the imager 18 such that the same general area is viewed from a different angle.

In some embodiments, defining an imager 18 in a perpendicular orientation to the movement control system 10100 (as shown in FIG. 6A) as having an a pitch and yaw of zero (i.e., as shown in FIG. 6A), the movement control system 10100 can allow both pitch and yaw adjustments relative to the binocular display unit 9 within the range of approximately ±60 degrees each, by approximately ±50 degrees each, by approximately ±40 degrees each, by approximately ±30 degrees each, by approximately ±20 degrees each, or approximately ±10 degrees each. In some embodiments, the pitch and yaw can have different adjustment ranges. For example, in some embodiments, the yaw can have an adjustment range of approximately ±40 degrees whereas the pitch can have an adjustment range of approximately three-quarters that of the yaw, one-half that of the yaw, one-quarter that of the yaw, or any other ratio between unity and zero. In some embodiments, the pitch can have an adjustment range of approximately ±20 degrees.

The adjustment range of yaw and pitch can correspond to the distance at full extension along both the x-axis and the y-axis. For example, in some embodiments, the pitch and yaw can be chosen such that the imager 18 can remain centered on the surgical site when the movement control system 10100 is fully extended in any direction. In some embodiments, the working distance between the imager 18 and the surgical site can be approximately 200 mm, with a range of translation along the x-axis of approximately ±175 mm, and a range of translation along the y-axis of approximately ±87.5 mm. In order to remain centered on the surgical site, the pitch adjustment range can be ±20 degrees and the yaw adjustment range can be ±40 degrees. As such, because the full extension need not be the same in both directions, the pitch and yaw adjustment ranges can also be different to match the differences in extension. In other embodiments, such as those in which the working distance can be adjusted, the pitch and yaw adjustment range can be chosen such that the imager 18 can remain centered on the surgical site when the movement control system 10100 is fully extended in any direction at at least one working distance. For example, in embodiments where the working distance can be adjusted between approximately 200 mm and 400 mm, the pitch and yaw adjustment range can be approximately ±20 degrees and approximately ±10 degrees respectively to allow centering at a working distance of 400 mm.

Additionally, in some embodiments, the imager 18 can adjust further in a "positive" angle than a "negative" angle. For example, the yaw may range from −5 degrees to 15 degrees.

As described in part above and as will be discussed in greater detail below, in some embodiments, increasing or decreasing the pitch and/or yaw of the imagers 18 relative to the binocular display unit 9 can be achieved by increasing or decreasing the pitch and/or yaw of the one or more control members, such as control member 10110. In some embodiments, the control member 10110 can be electrically coupled to the movement control system 10100 to provide pitch and yaw via an electromechanical system utilizing stepper motors, linear motors, or the like. For example, a joint of the control member 10110 can include components for detecting pitch and/or yaw of the control member 10110. In some embodiments, the joint of the control member 10110 can be gimbals which can detect pitch and/or yaw of the control member 10110. The signals from these sensors can be used to control other components of the movement control system, such as one or more electromechanical components such as stepper motors, linear motors, or the like to adjust the pitch and/or yaw of the imager 18. As should be appreciated by one of ordinary skill in the art, in some embodiments, the movement control system 10100 can be configured to allow rotation along other axes such as the z-axis. In some embodiments, the control member 10110 can be physically connected to the movement control system 10100 without any electromechanical assistance.

Additionally, in some embodiments, the movement control system 10100 can be configured to adjust the working distance between the imagers 18 and the surgical site. In some embodiments, the binocular display unit 9 can remain immobile while the working distance of the imagers 18 are adjusted. In some embodiments, the working distance can range from between approximately 1 m to approximately 10 mm, from between approximately 800 mm to approximately 50 mm, from between approximately 600 mm to approximately 100 mm, or from between approximately 400 mm to approximately 200 mm. In some embodiments, the control member 10110 can be electrically coupled to the movement control system 10100 to provide working distance adjustment via an electromechanical system utilizing stepper motors, linear motors, or the like. For example, a joint of the control member 10110 can include components for detecting rotation of the control member 10110 about the longitudinal axis. The signals from these sensors can be used to control other components of the movement control system, such as one or more electromechanical components such as stepper motors, linear motors, or the like to adjust the pitch and/or yaw of the imager 18. In some embodiments, the control member 10110 can be physically connected to the movement control system 10100 without any electromechanical assistance.

In some embodiments, the movement control system 10100 can include a translation system for translating an imager 18 and/or an imager arm, a pitch-yaw adjustment system for adjusting the pitch and/or yaw of the imager 18 and/or an imager arm, a control member, such as control member 10110, and one or more imager arms to which the imager 18 can be attached. In some embodiments, a working distance adjustment system can be included which can allow adjustments in working distance of the imager 18 and/or an imager arm. It should be appreciated by one of ordinary skill in the art that the translation system, the pitch-yaw adjustment system, and/or the working distance adjustment system can be used separately or in any combination.

Operation of the translation, pitch-yaw adjustment, and/or working distance adjustment systems can be performed using a control member, such as control member 10110. In some embodiments, control member 10110 can be operatively coupled to the translation, pitch-yaw adjustment, and/or working distance adjustment systems. For example, as described above, in some embodiments, the control member can be coupled to an electromechanical system for controlling the translation, pitch-yaw adjustment, and/or working distance adjustment systems. The control member can be directly attached to a component of the movement control system 10100 or can be remotely positioned (e.g., a toggle or joystick on a separate module). In some embodiments, the control member can be coupled directly to the translation, pitch-yaw adjustment, and/or working distance adjustment systems such that no electromechanical devices are used. In some embodiments, the operator can be given the option of controlling the translation, pitch-yaw adjustment, and/or working distance adjustment systems with or without electromechanical devices. For example, the operator can control the translation, pitch-yaw adjustment, and/or working distance adjustment systems without electromechanical devices for certain portions of a procedure and use such electromechanical devices for controlling the translation, pitch-yaw adjustment, and/or working distance adjustment systems during other portions of a procedure. As another example, in some embodiments coarse control of the movement control system 10100 can be achieved without use of electromechanical devices whereas fine control of the movement control system 10100 can be achieve with use of electromechanical devices, vice-versa, or a combination of the two.

In some embodiments, the movement control system 10100 can include a control system which controls functions of the electromechanical devices. In some embodiments, the electromechanical components can be programmed such that the electromechanical components can orient the translation, pitch-yaw adjustment, and/or working distance adjustment systems in certain positions based on the operator's input. For example, the electromechanical components can be programmed such that it goes to reverts back to a pre-set or previous position upon receiving a command from the operator. As another example, the electromechanical components can be programmed such that an operator can specify a desired position for the imager 18 and the control system can control the electromechanical devices coupled to the translation, pitch-yaw adjustment, and/or working distance adjustment systems orient the imager 18 in the desired position.

Figure 7:
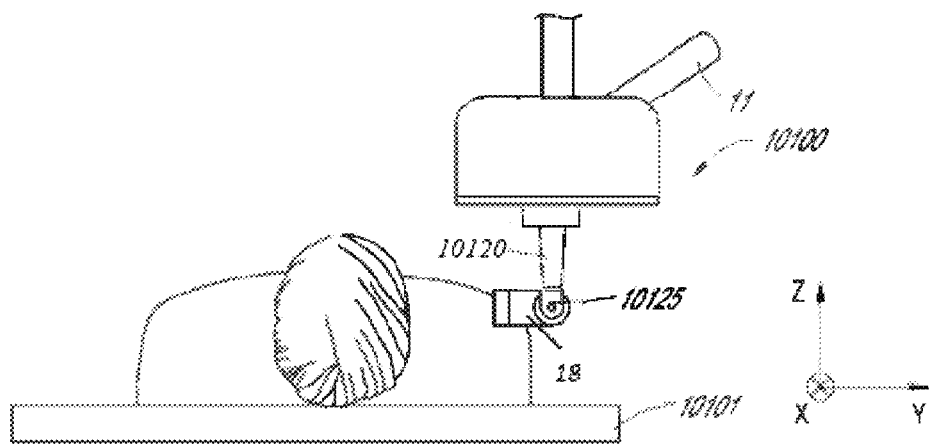
FIG. 7 is a side view of an embodiment of a surgical visualization system, a movement control system, and an imager.

With reference to FIG. 7, in some embodiments, the imager arm 10120 and the imager 18 can be attached such that the imager 18 can be directed towards the side of the head of a patient. For example, in some embodiments, the imager 18 can be attached to the imager arm 10120 using a yoke 10125 which can be designed to allow for coarse and/or fine control of pitch, yaw, and/or roll of the imager 18. In some embodiments, the yoke 10125 can have one or more pivots which can be configured to allow the imager 18 to have a viewing angle parallel to the operating room floor such that an operator can view the side of the head. In some embodiments, the yoke 10125 can be configured to allow the imager 18 to rotate such that the imager can be directed to a portion of the back of the head.

Figure 8:
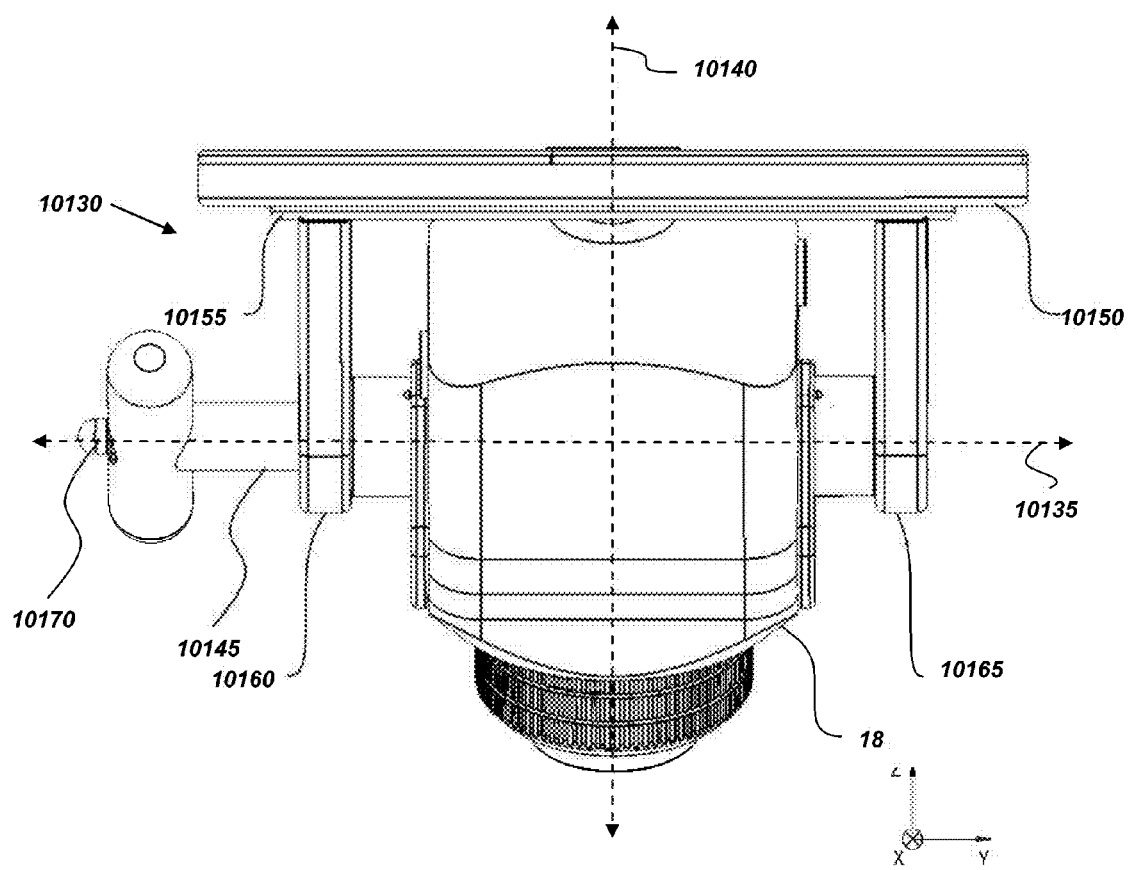
FIG. 8 is a rear view of an embodiment of an embodiment of a movement control system.

In some embodiments, the imager 18 can be positioned on a movement control system 10130 providing at least two rotational degrees of freedom and/or at least one translational degree of freedom. In some embodiments, movement control system 10130 can provide two rotational degrees of freedom and at least two translation degrees of freedom. For example, as shown in FIG. 8, the movement control system 10130 can allow for rotation along axis 10135 of the movement control system 10130 and/or along axis 10140 (which can be parallel with the z-axis). Moreover, as shown in the illustrated embodiment, the movement control system can allow translation along both the x-axis and y-axis. In some embodiments, apparatus 10130 can provide at least one translational degree of freedom.

As shown in the illustrated embodiment, the movement control system 10130 can include a one or more control members, such as control member 10145. Control member 10145 can be positioned such that the longitudinal axis of the control member 10145 is parallel with and/or collinear with axis 10135. This can advantageously allow the imager 18 to be rotated about axis 10135 by rotating the control member 10145. In some embodiments, the control member 10145 can be mechanically coupled to the imager 18. In some embodiments, the control member 10145 can be coupled to the imager 18 via an electromechanical system. For example, the control member 10145 can include sensors for detecting rotation of the control member 10145 and use data received from the sensors to rotate the imager 18 via electromechanical components such as stepper motors, linear motors, or the like.

As shown in the illustrated embodiment, the movement control system 10130 can include a first plate element 10150 and a second plate element 10155 which can be rotatable coupled. The second plate element 10155 can include first and second supports 10160, 10165 to which the imager 18 can be attached. In some embodiments, the first and second plate elements 10150, 10155 can be rotatable coupled such that the axis of rotation of the two plate elements 10150, 10155 is parallel and/or collinear with axis 10140.

In some embodiments, the control member 10145 can include one or more switches and/or actuators 10170 for controlling movement of the device. For example, the actuator 10170 can be coupled to mechanisms which can unlock the apparatus 10130 such that the movement control system 10130 can be manipulated to rotate and/or translate the imager 18. In some embodiments, the switches and/or actuators can be coupled to an electromechanical system to rotate and/or translate the movement control system 10130.

Optical Systems for Displays

FIGS. 9A-9D illustrate example display optical systems 11005 configured to provide a view of displays 11010 through oculars (not shown) that receive light from the last lens 11015 in the display optical system 11005. The display optical system 11005 forms an exit pupil at or near the entrance pupil of the surgeon binoculars. These pupils are closely matched, for example, in size and shape. In some embodiments, the exit pupil of the display optical system 11005 can be the same size or smaller than the entrance pupil of oculars used to view the display. The oculars form an exit pupil that is matched (e.g., in size and shape) to the entrance pupil of the surgeon's eye(s). In some embodiments, the display optical system 11005 is configured to produce a beam that has a relatively constant cross-section between the first lens element 11012 and the last lens element 11015, where the cross-section is relatively small. Advantageously, this allows the display optical system 11005 to be included in a relatively small or compact package and use relatively small optical elements. In some embodiments, the last lens 11015 collimates the beam leaving the display optical system 11005. The termination of the rays shown in FIG. 11A to the left of lens 11015 is the exit pupil of the display optical system 11005. In some embodiments, the exit pupil of the display optical system 11005 is configured to be the same size or smaller than, and positioned at the same location, as an entrance pupil of a binocular viewing assembly configured to allow a user to view the display 11010.

The lenses in the display optical system 11005 form a highly color-corrected view of the display by forming the exit pupil in a position favorably disposed for the user and the binoculars. A combination of singlets and bonded lenses provide such correction. The display optical system 11005 may be designed to provide such correction while keeping a small beam column or ray bundle, which permits adding mirrors and obtaining a compact package. In various embodiments, producing an undistorted image can be difficult without such a group of lenses designed properly to provide such correction. This correction includes both color correction as well as distortion correction.

The display optical system 11005 advantageously allows a relatively small, compact lens assembly to provide a view of a relatively large display 11010. The display optical system 11005 can be configured to work with displays 11010 of varying sizes, including, without limitation, displays with a diagonal that is less than or equal to about 0.86 in. (22 mm), at least about 0.86 in. (22 mm) and/or less than or equal to about 10 in., at least about 1 in. and/or less than or equal to about 9 in., at least about 2 in. and/or less than or equal to about 8 in., or at least about 4 in. and/or less than or equal to about 6 in. The display may, for example, have a diagonal of about 5 inches or about 8 inches in some embodiments. The total optical path length of the display optical system 11005 can be less than or equal to about 9 in., at least about 9 in. and/or less than or equal to about 20 in., at least about 10 in. and/or less than or equal to about 19 in., at least about 14 in. and/or less than or equal to about 18 in. The display optical system 11005 can include lenses, mirrors, prisms, and other optical elements configured to direct and manipulate light along an optical path. The display optical system 11005 can be used in conjunction with a primary display, a surgeon display, an assistant display, possibly other displays, or any combination of these.

Figure 9A:
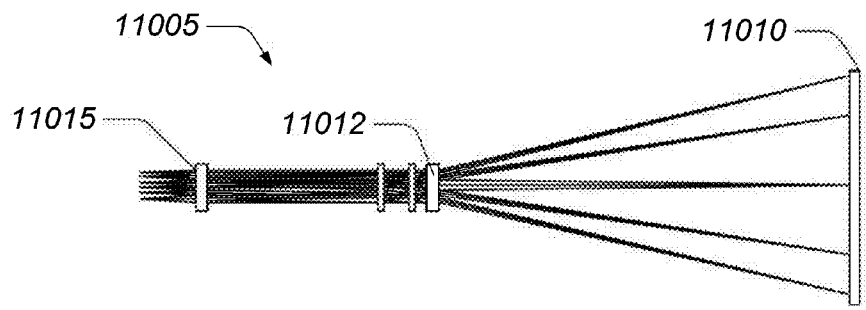
FIGS. 9A-9D illustrate example display optical systems configured to provide a view of a display or a pair of displays through oculars.

The example display optical system 11005 illustrated in FIG. 9A has a total optical path length of about 16.2 in. (412 mm). It is configured to provide an image of a 5 in. display 11010. The display optical system 11005 can include a lens 11012 configured to direct the light from the display 11010 along a path wherein light from the display 11010 is directed along a path with a relatively narrow cross-section. In various embodiments, the light received from the display is initially substantially reduced in beam size for example by the lens 11012 or lenses closest to the display and a more narrow beam is produced. In certain embodiments, for example, the lens 11012 or lenses closest to the display collect light at an angle (half angle) in excess of 20°, 25°, 30° and reduce the beam size of the light. This design is advantageous because it allows for the elements in the display optical system 11005 to be relatively small and compact. In some embodiments, the cross-section of the optical beam after the lens 11012 in the display optical system 11005 can be configured to be relatively constant. This configuration allows folding or redirecting mirrors present in the optical path to remain small.

Figure 9B:
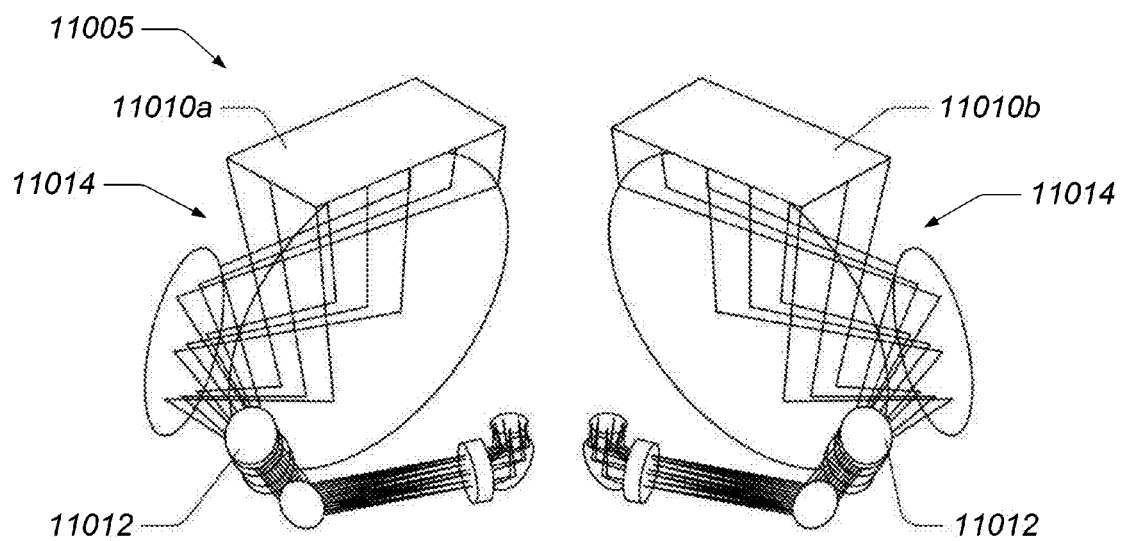

FIG. 9B illustrates a binocular display optical system 11005 configured to provide a view of stereo displays 11010a, 11010b through a pair of oculars. The binocular display optical system 11005 can be based on the optical design illustrated in FIG. 9A, and can include one or more elements 11014 in the optical path before the lens 11012 to reduce the physical size of the optical system while maintaining the length of the optical path. These elements can include mirrors, prisms, and/or other optical elements configured to redirect the light from the displays 11010a, 11010b to the lens 11012. In some embodiments, the elements 11014 include curved mirrors which redirect the optical path and converge the rays from the displays 11010a, 11010b. In some embodiments, the elements 11014 include mirrors or prisms (for example that may have planar reflecting surface) that do not substantially affect the convergence of the light rays, but redirect the optical path. In some embodiments, because of the shape of the beam incident on the reflective surface, for example, mirror, the reflective surface or cross-section of the mirror is non-circular, and is, for example, elliptical. Accordingly, in various embodiments the cross-section of the mirror or other reflective surface is possibly being longer in one direction than in another, for example, orthogonal direction. These elements may fold the optical path to provide for a more compact system. Such a system may therefore have an optical path length from display to ocular that is longer than the length and/or width of the viewing platform of the combination thereof.

In some embodiments, the display optical system 11005 can include at least four mirrors, or less than or equal to four mirrors. In certain implementations, two mirrors can be used to fold the optical path from the display 11010 to the exit pupil, the two mirrors positioned between the first lens 11012 and the display 11010. In some embodiments, the display optical system 11005 includes at least four lenses or less than or equal to four lenses.

Figure 9C:
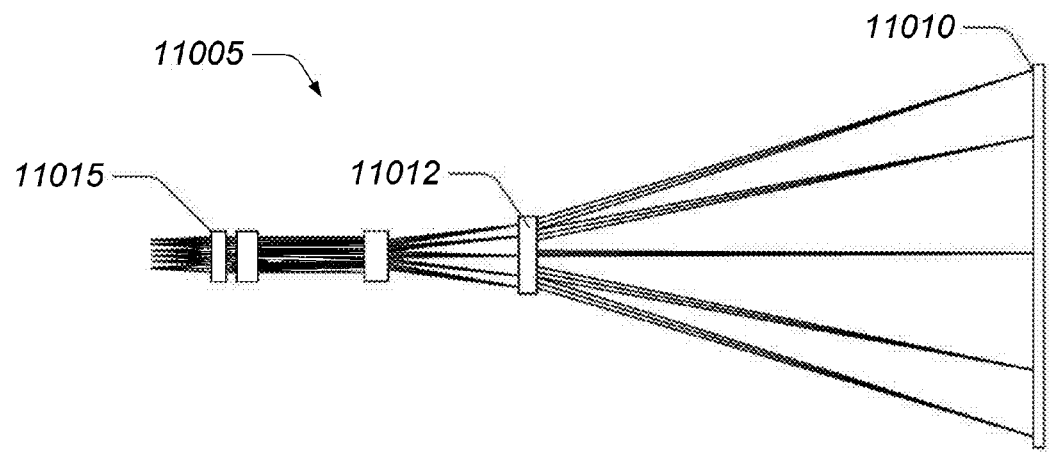

The example display optical system 11005 illustrated in FIG. 9C has a total optical path length of about 18.7 in. (475 mm). It is configured to provide an image of an 8 in. display 11010. The display optical system 11005 can include a lens 11012 configured to direct the light from the display 11010 along a path wherein light from the display 11010 is directed along a path with a relatively narrow cross-section, allowing for the display optical system 11005 to be relatively small and compact. In some embodiments, the cross-section of the optical beam after the lens 11012 in the display optical system 11005 (e.g., to the exit pupil prior to the entrance to a binocular viewing assembly) can be configured to be relatively constant. This configuration allows folding or redirecting mirrors present in the optical path to remain small. The display optical system 11005 can be configured to be used in conjunction with a display 11010 with a relatively high resolution.

Figure 9D:
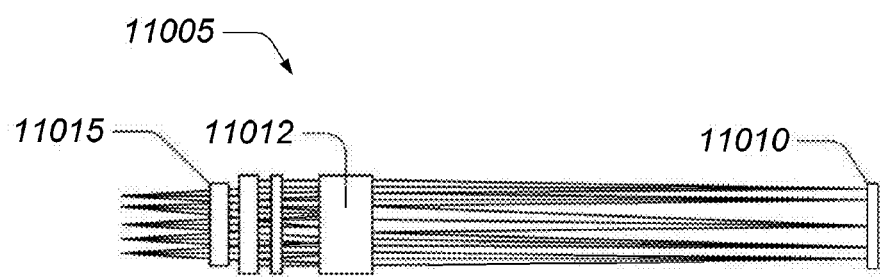

The example display optical system 11005 illustrated in FIG. 9D has a total optical path length of about 9.3 in. (237 mm). It is configured to provide an image of a smaller display, in this case a 0.9 in. (22 mm) display 11010. Because the display is much smaller than the display in the embodiments described in connection with FIGS. 9A-9C, the optical path can be much shorter and may fit into a smaller space. The display optical system 11005 can include a lens 11012 configured to direct the light from the display 11010 along a path wherein light from the display 11010 is directed along a path with a relatively narrow cross-section, allowing for the display optical system 11005 to be relatively small and compact. In some embodiments, the cross-section of the optical path after the lens 11012 in the display optical system 11005 can be configured to be relatively constant. This configuration allows folding or redirecting mirrors present in the optical path to remain small. Based at least in part on the relatively short optical path length, the display optical system 11005 can be configured to be used in conjunction with a secondary display or an assistant display.

Figure 10A:
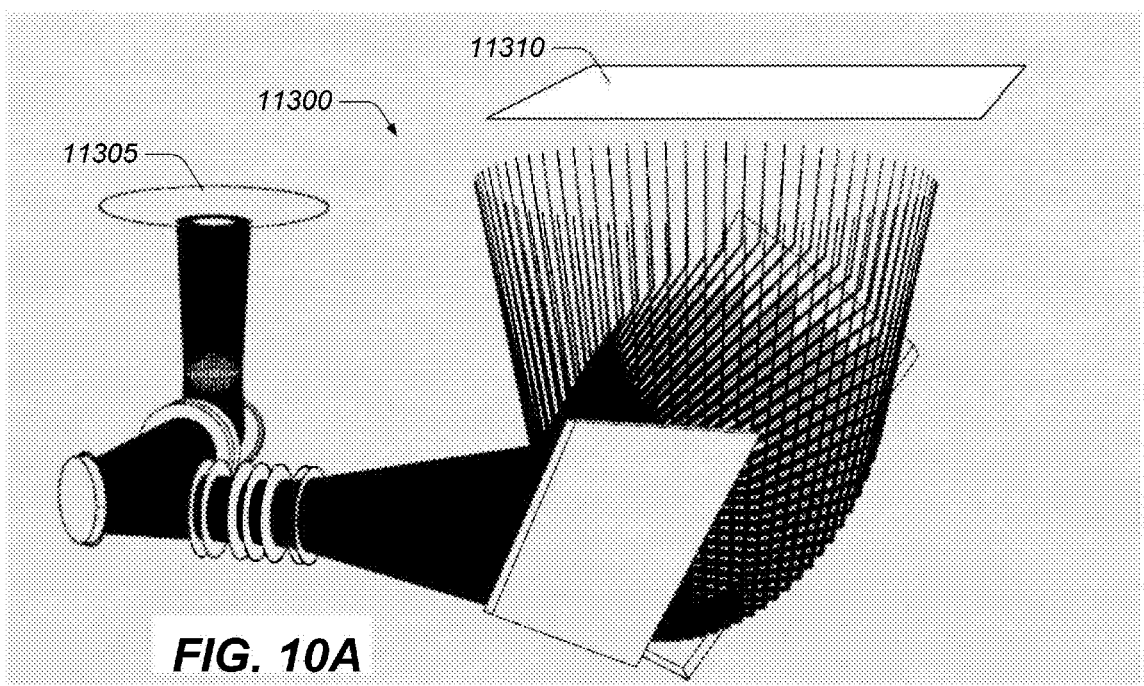
FIGS. 10A-10G illustrate example display optical systems configured to deliver to oculars images of a display wherein light paths that would intersect a viewing assembly are reduced or eliminated through baffles.
Figure 10B:
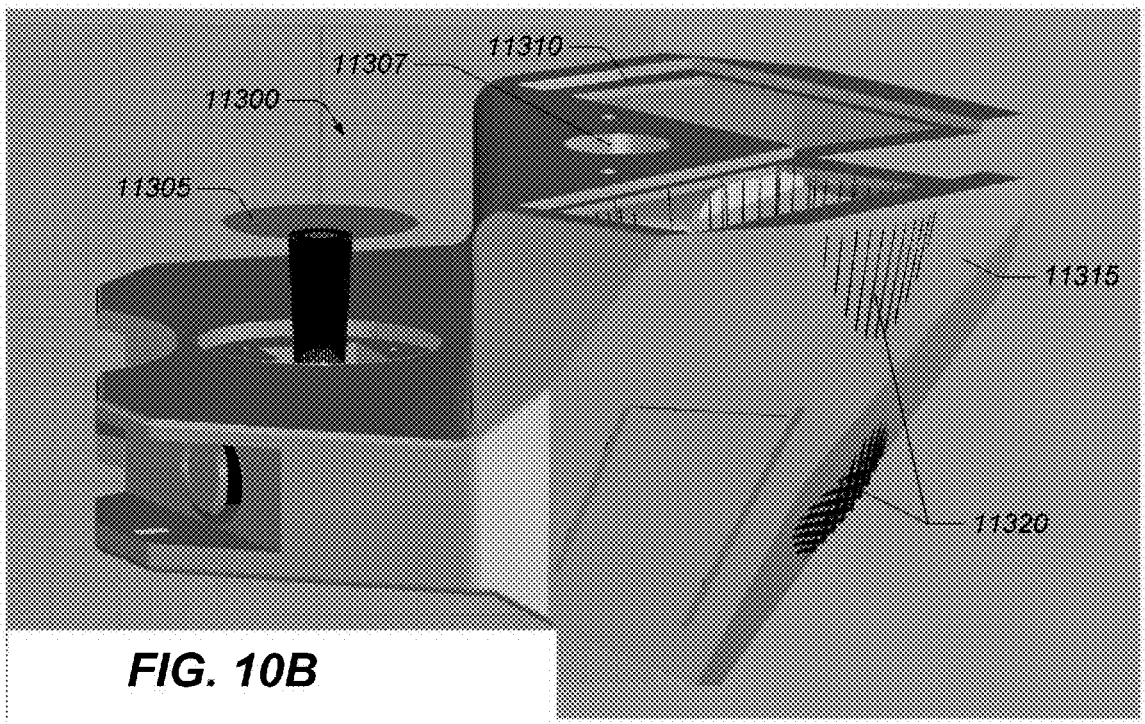

FIGS. 10A-10G illustrate example display optical systems 11300 configured to provide a view of a display 11310, the display optical system 11300 having an exit pupil 11305 wherein light paths that would intersect a viewing assembly housing 11315 are reduced or eliminated through baffles or apertures 11320, where a baffle includes a panel with an aperture. FIG. 10A illustrates an example embodiment of a display optical system 11300 comprising a display 11310, with other optical components configured to direct the light from the display 11310 to the exit pupil 11305. The light paths are traced with black lines to show the periphery of the bundle of light paths from the display 11310 to the exit pupil 11305. FIG. 10B shows this same display optical system 11300 as situated in an example viewing assembly housing 11315. When the display optical system 11300 is configured in this way, portions of the light 11320 from the display 11310 are outside of the housing 11315, which leads to light being reflected and/or scattered off the sidewalls of the housing along the path to the exit pupil 11305. This can lead to undesirable results, such as degradation in the quality of the image of the display 11310 viewed with an ocular, for example, by reducing contrast. The display optical systems 11300 can be configured to provide a collimated beam at the exit pupil 11305 such that a binocular viewing assembly comprising an objective and oculars can mate to the viewing assembly housing 11315 and view the display 11310.

Figure 10C:
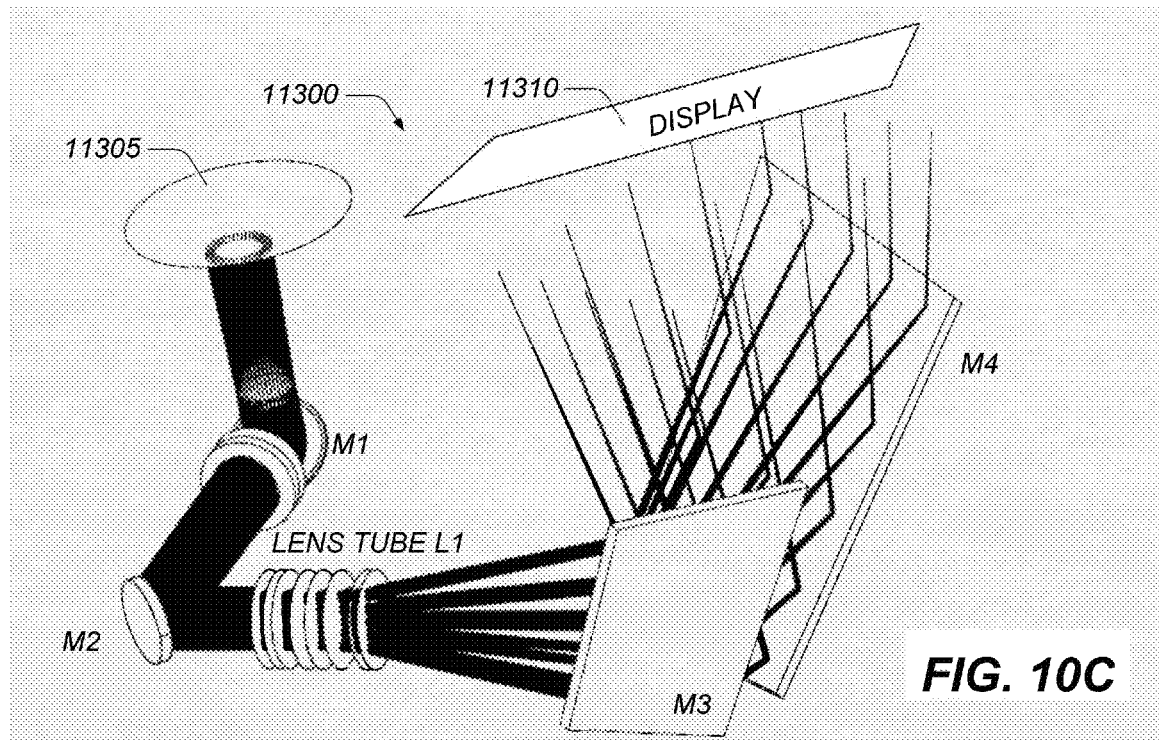
Figure 10D:
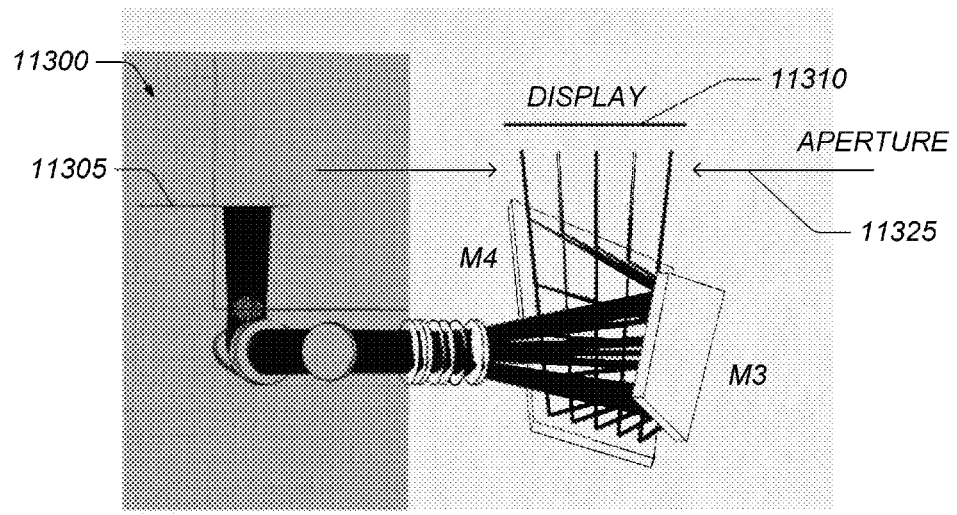
Figure 10E:
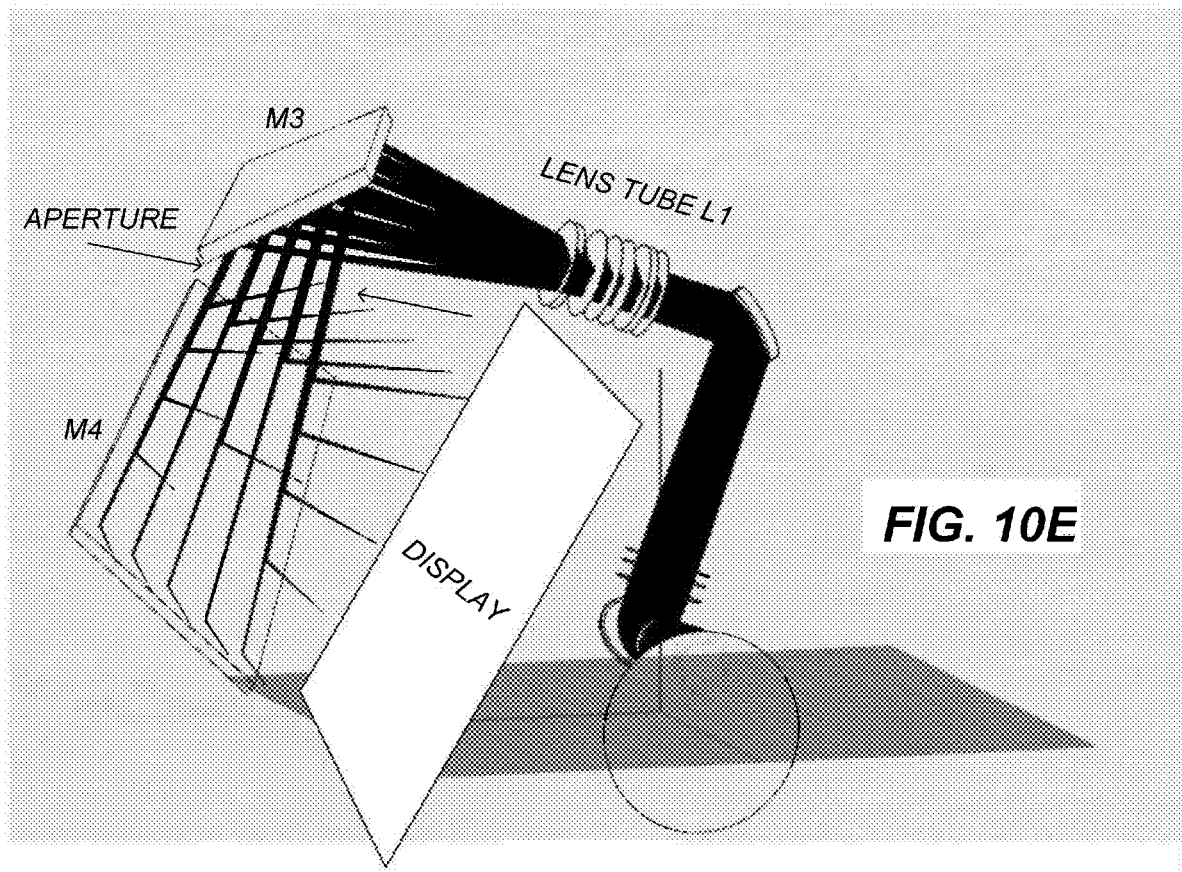
Figure 10F:
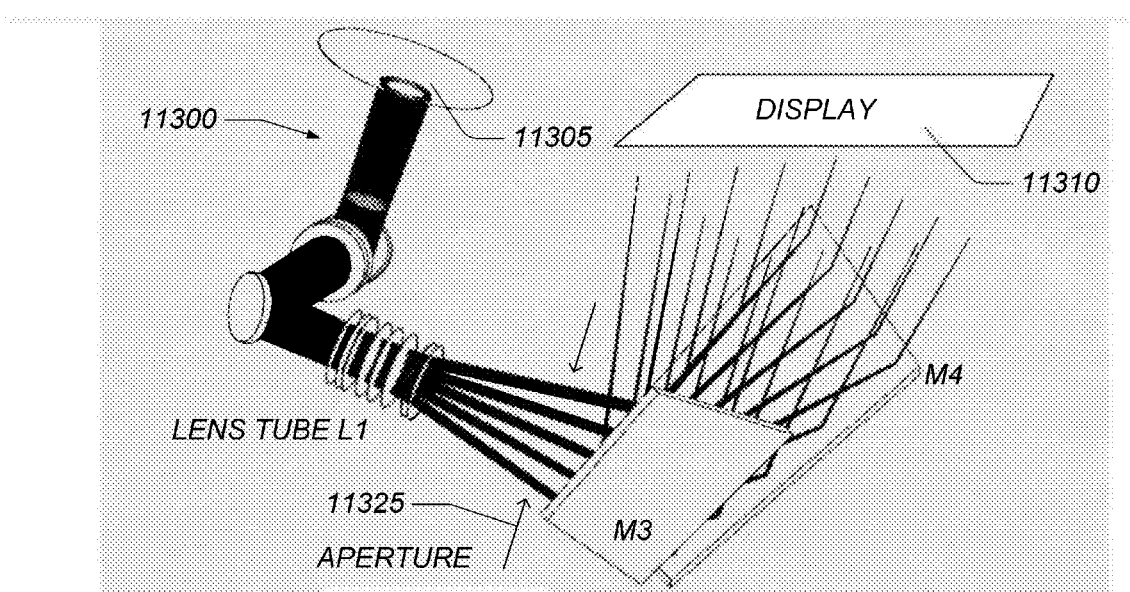

In some embodiments, one or more baffles or apertures 11325 can be incorporated into the display optical system 11300 to reduce or eliminate the amount of light that intersects with the housing 11315. The apertures may be disposed to reduce the view of the sidewalls by the ocular, thereby reducing the light collected that is reflected off the sidewalls. FIG. 10C illustrates an example embodiment of the display optical system 11300 without any apertures. The display optical system includes mirrors M1, M2, M3, and M4 to redirect the light path within in the viewing assembly. The mirrors M1, M2, M3, and M4 fold the optical path such that the display optical system 11300 can be contained in a more compact housing having a smaller footprint. Additionally in various embodiments, the mirrors M1, M2, M3, and M4 fold the optical path wraps around a supporting column configured to support the housing on an arm. In various embodiments the column is a conduit for electrical signals, power, and illumination fibers. Electronics boards, for example, with FPGAs, etc., can be disposed on the top of the display. Such a configuration may be useful because signal integrity (e.g. of MIPI2 signal) can be preserved with short cable routing. An opening 11307 for the support column about which the optical path is wrapped is visible in FIG. 10B. The display optical system includes lenses in lens tube L1 to shape (e.g., collimate) the light path along the path from the display 11310 to the exit pupil 11305. The lens tube L1 can be used to maintain a relatively narrow optical passageway that contains substantially all of the light travelling from the display 11310 to the exit pupil 11305. FIG. 10D illustrates the example embodiment of the display optical system 11300 from FIG. 10C with an aperture 11325 added between the mirror M4 and the display 11310. FIG. 10E illustrates the example embodiment of the display optical system 11300 from FIG. 10C with an aperture 11325 added between the mirror M3 and the final mirror M4. FIG. 10F illustrates the example embodiment of the display optical system 11300 from FIG. 10C with an aperture 11325 added between the lens tube L1 and the mirror M3.

Figure 10G:
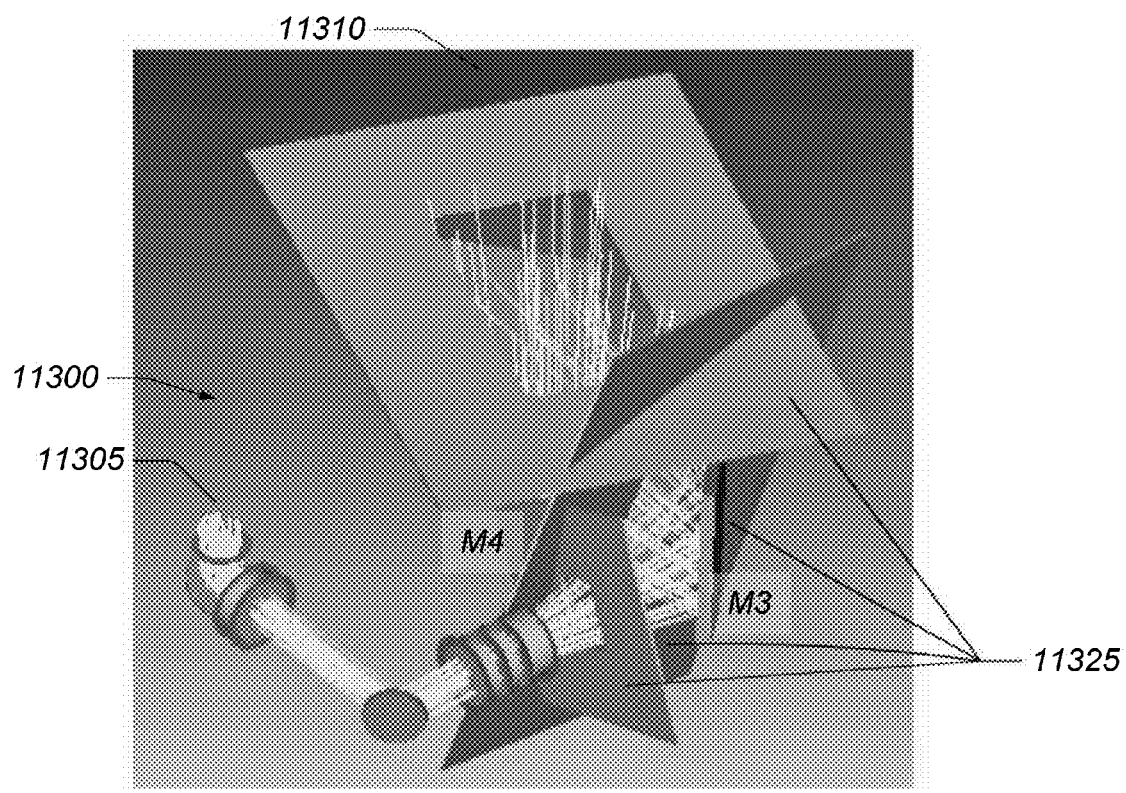

FIG. 10G illustrates the example embodiment of the display optical system 11300 from FIG. 10C, with apertures 11325 added at all the locations illustrated in FIGS. 10D to 10F, between the lens tube L1 and the mirror M3, between the mirror M3 and the mirror M4, and between the mirror M4 and the display 11310. Simulations of the performance of this configuration have shown that the radiant intensity of unwanted light, e.g., light that arrives after being reflected or scattered from the inner housing of the housing 11315, have been reduced by about 3.6× while the radiant intensity at the exit pupil 11305 from the display 11310 has been substantially held constant which substantially means that there is less than a 10% change in the radiant intensity.

In some embodiments, the display optical system 11300 can include at least four baffles or less than or equal to four baffles. In certain implementations, four baffles can be included in the optical path between the first lens and the display 11310. In some implementations, two mirrors can be included in the optical path between the first lens and the display 11310. In some embodiments, the optical path can include, in order from the display 11310, a first baffle, a first mirror, a second baffle, a second mirror, and a third baffle prior to the first lens.

In some embodiments, the display can be a curved surface, for example either a projection display or recent generation of flexible LCD or OLED displays having high-resolution (e.g., in excess of 300 ppi). A curved display may provide two advantages: the imaging optics for the display can be less complex than for flat panels, and the cone or numerical aperture of each picture element in the display can be directed towards the viewing optics and in the periphery of the display, thereby providing a brighter image less subject to vignetting.

In some embodiments, the display can be a volumetric display comprising two or more transmissive display panels having a single backlight wherein the transmissive display panels are stacked to provide different planes of focus for a surgeon. The transmissive displays can be active matrix liquid crystal displays ("AMLCD") or other types of transmissive displays. The backlight can be a fluorescent lamp, LEDs, or other suitable light source. By having displays positioned in different focal planes, image data from different focal planes may be presented to the surgeon with relatively less image processing and/or compression compared to a system which combines data from multiple focal planes into a single image. In some embodiments, a number of cameras can be positioned at varying depths or having varying focal distances such that the displays at different focal planes are configured to display image data from cameras positioned or focused at different depths to create a display that assists the surgeon in identifying positions of features within displayed images.

The display can show, as an overlay, pre-operative CT, MR, or other 3D image datasets from, for example, conventional surgical navigation systems (e.g., the Medtronic StealthStation or Treon, Stryker Surgical Navigation System, or Brainlab, among others). In various embodiments, in addition to images, the display can additionally provide numerical data and/or text. For example, in various embodiments, the display can overlay information such as distance or tool measurements, transparent tool renderings, camera identification information (e.g., the portion of the composite image attributable to a specific optical sensor may generate an identifying border around that portion), up/down orientation, elapsed time, and/or one or more still images captured from one or more optical sensors from a previous time in the operation The tracking system can provide 5-DOF (degrees of freedom) or 6-DOF position and orientation information to conventional surgical navigation systems. Other information, graphic, alpha numeric, or otherwise, can be provided.

The tool image can be magnified with respect to the wide-field view image, and change in image scaling will occur as the tool is moved in and out. In some embodiments, a visual metaphor for embodiments of the display is that of a hand-held magnifying glass for inspecting and doing work on a smaller region of a larger workpiece, while seeing the larger workpiece with lower magnification (if any) in more peripheral regions of the visual field to provide situational awareness. Tool images, for example, can be superimposed on the background image thereby blocking that portion of the background image. In various embodiments, the tool images may be stereo.

In some embodiments fluorescence information can be displayed. Cameras that image in different wavelengths, such as infrared, could image the surgical site or objects contained therein. In some embodiments, features could be made to fluoresce, for example, by injecting fluorescent chemical and illuminating the area with light the will induce fluorescence. Such a technique may be useful to identify and/or highlight the location and/or boundaries of specific features of interest such as tumors, etc. The fluorescence or other wavelength of interest may be detected by the one or more cameras imaging the surgical field such as one or more camera providing a surgical microscope view. In some embodiments, images produced by fluorescence or other wavelengths of interest are superimposed on one or more images from other camera(s). Filtering could be provided to remove unwanted wavelengths and possibly increase contrast. The filter can remove excitation illumination. In some embodiments emission image content, (e.g., fluorescing tissue) can be parsed and superimposed on image content that is not emitting (e.g., tissue that is not fluorescing), or vice versa. In various embodiments, such as where the fluorescing wavelength is not visible (e.g., for fluorescence in the infrared), an artificial color rendition of the fluorescing content can be used in place of the actual fluorescing color so as to enable the fluorescing tissue to be visible.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate embodiments also can be implemented in combination in a single embodiment. Conversely, various features that are described in the context of a single embodiment also can be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

What is claimed is:

1. A medical apparatus comprising:
   at least one video camera configured to acquire video images of a surgical site, said at least one video camera being a surgical microscope camera having a field of view that can be configured to include the surgical site, wherein the surgical microscope camera is configured to provide a surgical microscope view of the surgical site;
   a display housing; and
   a plurality, of electronic displays disposed within the display housing, each of the plurality of electronic displays comprising a plurality of pixels configured to produce a two-dimensional image, at least one of the electronic displays is configured to produce a two-dimensional image from said surgical microscope camera,
   wherein the plurality of electronic displays are configured to present superimposed images in a field of view of a person's eye, the superimposed images comprising at least one image from a first electronic display of the plurality of electronic displays and at least one image from a second electronic display of the plurality of electronic displays, the second electronic display different from the first electronic display, and
   wherein said surgical microscope camera is not coupled to a direct view surgical microscope.

2. The medical apparatus of claim 1, wherein at least one of the plurality of electronic displays comprises a transmissive display panel.

3. The medical apparatus of claim 1, wherein the superimposed images comprise a video of a first portion of a surgery site that is superimposed on a video of a second portion of the surgery site, the first portion contained within the second portion.

4. The medical apparatus of claim 3, wherein the video of the first portion is magnified relative to the video of the second portion.

5. The medical apparatus of claim 1, further comprising a binocular viewing assembly comprising the display housing.

6. The medical apparatus of claim 5, wherein said binocular viewing assembly further comprises a plurality of oculars, the plurality of oculars configured to provide views of the plurality of electronic displays disposed within the display housing, the plurality of oculars comprising a left ocular and a right ocular, each ocular being tubular.

7. The medical apparatus of claim 5, further comprising:
   a viewing articulating arm, the binocular viewing assembly disposed on the viewing articulating arm, the viewing articulating arm configured to adjust a position of the binocular viewing assembly; and
   a second articulating arm, the surgical microscope camera disposed on the second articulating arm so that the surgical microscope camera can be positioned independently of the binocular viewing assembly.

8. The medical apparatus of claim 5, wherein the surgical microscope camera is smaller than the binocular viewing assembly.

9. The medical apparatus of claim 6, wherein said binocular viewing assembly is configured not to provide a surgical microscope view via an optical path from an ocular of said plurality of oculars through an aperture in said housing that creates a pathway to the surgical site.

10. The medical apparatus of claim 6, wherein the surgical microscope camera has an optical input for receiving light from the surgical site and the distance from the plurality of oculars to the optical input of the surgical microscope camera is not larger than the size of the binocular viewing assembly such that when in use, a surgeon can ergonomically perform surgery at a surgical site beneath the surgical microscope camera while viewing through the plurality of oculars the images displayed on the plurality of electronic displays.

11. The medical apparatus of claim 1, further comprising an external monitor.

12. The medical apparatus of claim 11, wherein the external monitor is disposed on an arm.

13. The medical apparatus of claim 1, further comprising two external monitors.

14. The medical apparatus of claim 13, wherein at least one of the two external monitors is disposed on an arm.

* * * * *